United States Patent [19]
Ylihonko et al.

[11] Patent Number: 5,986,077
[45] Date of Patent: Nov. 16, 1999

[54] PROCESS FOR PRODUCING ANTHRACYCLINES AND INTERMEDIATES THEREOF

[75] Inventors: Kristiina Ylihonko; Juha Hakala; Pekka Mäntsälä, all of Turku, Finland

[73] Assignee: Galilaeus Oy, Pilspanrlstl, Finland

[21] Appl. No.: 08/809,740

[22] PCT Filed: Sep. 29, 1995

[86] PCT No.: PCT/FI95/00537

§ 371 Date: Mar. 27, 1997

§ 102(e) Date: Mar. 27, 1997

[87] PCT Pub. No.: WO96/10581

PCT Pub. Date: Apr. 11, 1996

[30] Foreign Application Priority Data

Sep. 30, 1994 [FI] Finland ................................. 944556

[51] Int. Cl.$^6$ ................... C07H 21/04; C12P 1/04; C12N 15/31; C12N 15/76
[52] U.S. Cl. ........................ 536/23.1; 435/41; 435/128; 435/320.1
[58] Field of Search ................. 536/23.1, 24.1; 435/172.1, 320.1, 41, 69.1, 148

[56] References Cited

U.S. PATENT DOCUMENTS 5,364,781  11/1994  Hutchinson et al. ............... 435/193
5,672,491   9/1997  Khosla et al. ...................... 435/148

FOREIGN PATENT DOCUMENTS 933200     7/1993  Finland .
WO 92/16629 10/1992  WIPO .

OTHER PUBLICATIONS

Lampel et al., Transformation and Transfection of Anthracycline–Producing Streptomyces. Applied and Environmental Microbiology. 51 (1): 126–131, Jan. 1986.

Niemi et al. Hybrid Anthracycline Antibiotics: Production of New Anthracyclines by Cloned Genes from Streptomyces purpurascens in Streptomyces galilaeus. Microbiology. 140 (6): 1351–1358, May 1994.

Bibb, Mervyn J. et al., "Analysis of the nucleotide sequence of the Streptomyces glaucescens tcml genes provides key information about the enzymology of polyketide antibiotic biosynthesis", EMBO Journal, vol. 8, No. 9, pp. 2727–2736 (1989).

Yu, Tin–Wein et al., "Cloning, Sequencing, and Analysis of the Griseusin Polyketide Synthase Gene Cluster from Streptomyces Griseus", Journal of Bacteriology, vol. 176, No. 9, May 1994, p. 2627–2634 (1994).

Malpartida, F. et al., "Homology between Streptomyces Genes Coding for Synthesis of Different Polyketides used to Clone Antibiotic Biosynthetic Genes", Nature, vol. 325, pp. 818–821 (1987).

McDaniel, Robert et al., "Engineered Biosynthesis of Novel Polyketides" Science, vol. 262, pp. 1546–1550 (1993).

McDaniel, Robert et al., "Engineered Biosynthesis of Novel Polyketides: Manipulation and Analysis of an Aromatic Polyketide Synthase with Unproven Catalytic Specificites" American Chemical Society, vol. 115, pp. 11671–11675 (1993).

Stutzman–Engwall, Kim J., "Multigene Families for Anthracycline Antibiotic Production in Streptomyces Peucetius" Natl. Acad. Sci. USA, vol. 86, pp. 3135–3139 (1989).

*Primary Examiner*—Nancy Degen
*Attorney, Agent, or Firm*—Evenson, McKeown, Edwards & Lenahan, P.L.L.C.

[57] ABSTRACT

A process for producing anthracyclines and intermediates thereof expressing in a foreign Streptomyces host a DNA fragment relating to the biosynthetic pathway of anthracyclines and, if desired, intermediates obtained may be converted to anthracyclines or aglycones thereof using e.g. non-producing Streptomyces mutant strains.

14 Claims, 9 Drawing Sheets

A) (starting unit: propionate)
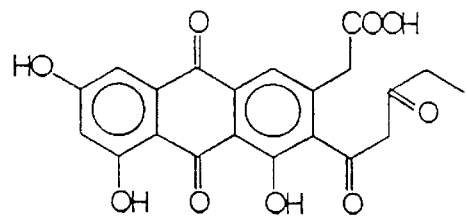
2-OH-aklanone acid (H061)
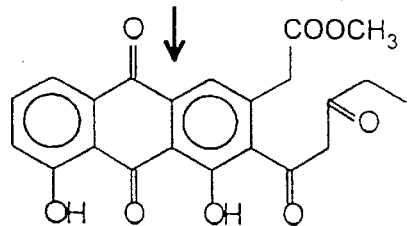
Methyl ester of aklanone acid (H036)
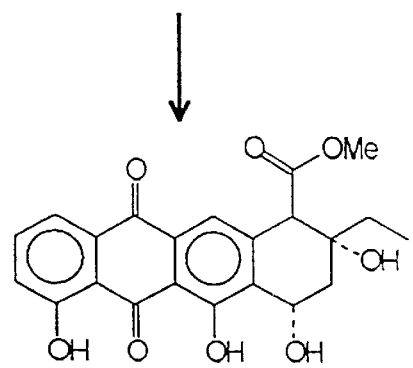
Aklavinone (H039)
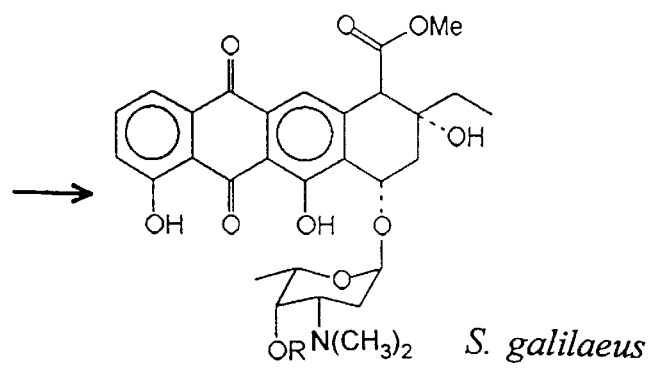
Aclacinomycin  *S. galilaeus*
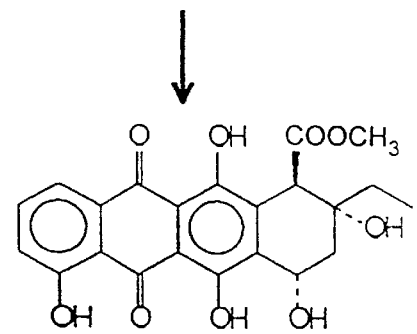
ε-rhodomycinone
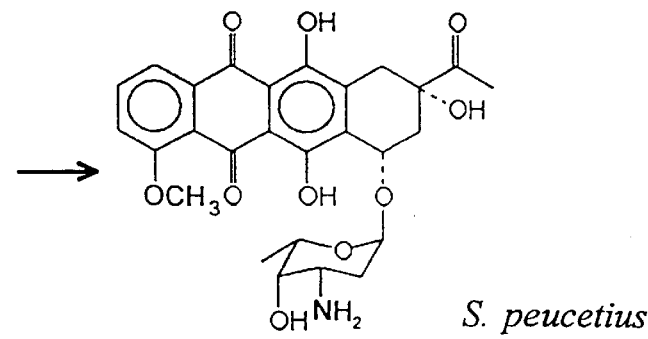
Daunorubicin  *S. peucetius*
Fig. 1A/1

ε-rhodomycinone
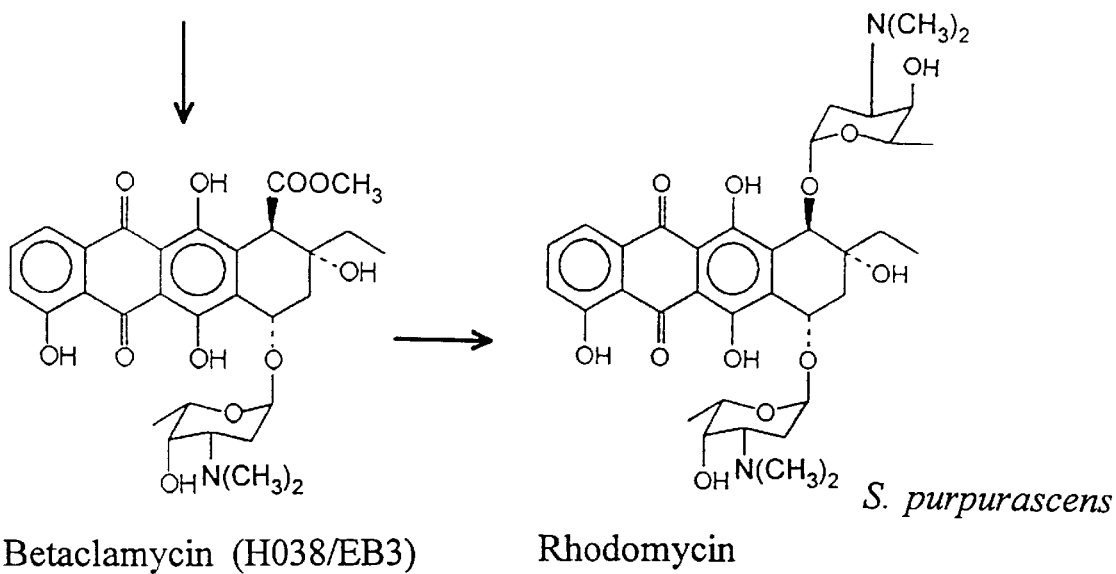
Betaclamycin (H038/EB3)  Rhodomycin
Fig. 1A/2

B) (starting unit: acetate)

Steffimycin

Nogalamycin

= pIJ486 (6.2 kb)

= pSY15 insert (12 kb)

PROCESS FOR PRODUCING ANTHRACYCLINES AND INTERMEDIATES THEREOF

FIELD OF INVENTION

The present invention pertains to a process for producing anthracyclines and intermediates thereof by expressing in a foreign host a DNA fragment relating to the biosynthetic pathway of anthracyclines and, if desired, the intermediates obtained are converted to anthracyclines or aglycones thereof using non-producing mutant strains.

RELATED ART

Polyketide antibiotics are a broad and variable group of compounds which are composed of poly-$\beta$-ketomethylene chain $[CHRO]_{4-20}$. A common feature of poly-ketides is their biosynthetic route which is similar to the biosynthesis of fatty acids. Katz, L. and Donadio, S. (1993) have recently published a review article concerning polyketides. As their structure the antibiotics of anthracycline group are aromatic polyketides, the common structural body of which is 7,8,9,10-tetrahydro-5,12-naphthacene kinone of the general formula (A)

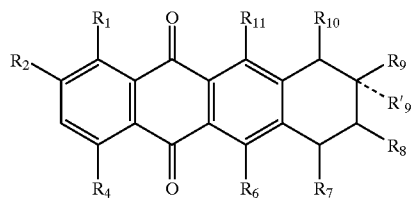

To this structural body one or more sugars and other substituents are attached. The structural body of the molecule, to which the sugars are attached, is called an aglycone. Anthracyclines are discussed more specifically e.g. in the article of A. Fujiwara and T. Hoshino (1986). Several anthracyclines are cytostatically active and thus they are of continuous interest.

To find new anthracyclines screening of Streptomyces bacteria from the soil and mutation thereof are used. To modify known anthracyclines synthetic methods have been used, whereby chemical groups are added to or removed from either the aglycone or the sugar moiety. Similarly, biotransformation is used, wherein in living cells molecules are modified which have been produced by other production strains or by synthetic methods. Some anthracyclines have also been produced by synthetic methods.

The hybrid antibiotic technology has been disclosed as a new technology in the preparation of new antibiotics. It has been established to comprise production by genetic engineering of molecules which have structural features of natural products of two strains. The process is described in the publication of H. G. Floss: "Hybrid antibiotics—the contribution of the new gene combinations" (1987). The hybrid antibiotic technology gives an opportunity to controlled production of new compounds.

Cloning of actinorhodin genes from *Streptomyces coelicolor* (Hopwood et al., 1985) can be considered as the pioneer work in the molecular biological study of polyketide antibiotics and at the same time of streptomycetes. In 1987 Malpartida et al. reported about the hybridization of different polyketide producers to the actI and actIII DNA fragments and thereafter genes of the polyketide synthase (PKS) domain have been identified in many Streptomyces species exploiting the homology. Sequencing of these genes has shown that the genes are strongly conserved and include three Open Reading Frames, ORF 1, 2 and 3. The products of these three genes are needed for the formation of the linear polyketide bound to the enzyme complex. For the optimal formation of the correct product encoded by the PKS-genes five ORFs are needed in tetracenomycin (Shen and Hutchinson, 1993). The sequenced aromatic PKSs are given in Table 1.

TABLE 1

Cloned and sequenced gene domains encoding polyketide synthase of aromatic polyketide antibiotics

| Strain | Product | Reference |
| --- | --- | --- |
| S. coelicolor | aktinorhodin | Fernandez-Moreno, M. A. et al. 1992 |
| | | Hallam, S. E. et al. 1988 |
| S. violaceoruber | granaticine | Sherman, D. H. et al. 1989 |
| S. glaucescens | tetracenomycin | Bibb, M. J. et al. 1989 |
| S. rimosus | oxitetracycline | Kim, E-S. et al. 1994 |
| S. cinnamonensis | monoensine | Arrowsmith, T. J. et al. 1992 |
| S. griseus | griseusine | Yu, T-W. et al. 1994 |
| S. roseofulvus | frenolisine | Bibb, M. J. et. al. 1994 |

Polyketide synthase (PKS) is a multienzyme complex which functionally reminds the synthase of long chain fatty acids. The separate components of actinorhodin PKS are so called actORF1 ketoacyl synthase (KS); actORF2 homologous to KS may effect on the length of the polyketide chain (McDaniel, R., et al., 1993); actORF3 acyl carrier protein (ACP); actORF5 ketoreductase (KR) and actORF4 cyclase/dehydrase, which may be responsible for the aromatization of the first ring.

The most part of the biosynthetic anthracyclines are formed via the aklavinone intermediate phase, whereafter the compound is glycosylated or it is modified by adding e.g. hydroxyl or methyl groups. Modifications can occur also after the glycosylation. The biosynthesis of aklavinone and anthracyclines which are further formed therefrom are described e.g. in "Advances in bioconversion of anthracycline antibiotics" (1989) of U. Gräfe et al, and in the references cited therein. The biosynthetic route of the nogalamycin aglycone being formed of ten acetates is evidently analogous to the biosynthesis of aklavinone. (FIGS. 1A and 1B).

DESCRIPTION OF THE INVENTION

A DNA fragment cloned from *Streptomyces nogalater* can be used according to this invention to combine the different phases of the biosynthetic route of anthracyclines, whereby hybrid anthracyclines and precursors of anthracyclines can be produced. This happens by transferring the cloned DNA fragment to a Streptomyces strain which produces anthracyclines or, alternatively, to a non-producer of anthracyclines.

The DNA fragment of *Streptomyces nogalater* including in the biosynthesis of anthracycline and being cloned according to this invention caused surprisingly production of anthracycline precursors in *S. lividans*, a host which does not produce anthracyclines. On the basis of the structures of the compounds obtained, the DNA fragment was supposed to include most of the genes needed for the biosynthesis of anthracycline aglycones. By complementation of mutant strains, analyzing the hybrid products and sequencing the DNA fragments we have been able to show that the DNA fragment comprises the activity responsible for the election of the starting unit which defines the side chain of the 9-position (*S. galilaeus* hybrid products), the polyketide synthase genes, the gene of the enzyme which is needed for removing the hydroxyl in 2-position, (ketoreductase), the methyl transferase gene needed for the carboxylic acid esterification, the mono-oxygenase gene.

This DNA fragment and anthracycline precursors produced by it have further been used to produce hybrid anthracyclines.

The present invention enables one to produce some known cytostatically active anthracyclines (auramycins) as well as prior unknown compounds. Use of the polyketide synthase of anthracyclines in the production of hybrid anthracyclines has not been described previously, neither the change of the starting unit of polyketide synthesis by transferring genes to a foreign host. Further, there is no prior disclosure of the cloning of genes of the biosynthetic pathway of nogalamycin produced by *S. nogalater*, or use thereof.

The similarity of the biosynthetic genes of polyketide antibiotics disclosed by Malpartida et aL (1987) was the starting point to the discovery of the biosynthetic genes of nogalamycin. The total DNA of *S. nogalater* being cleaved by suitable restriction enzymes was hybridized by the Souther-techniques to the actI probe, and thus two hybridizing DNA fragments were obtained. In an optimal case a suitable probe shows one DNA fragment. The use of cross hybridization was, however, considered to be possible as a strategy in identifying the biosynthetic genes, because the signals were strong.

The strategy by which the DNA fragment according to the invention was found was the following: A fragment homologous to the actI fragment described by Malpartida et al. (1987) was isolated from *S. nogalater*. Said homologous fragment and flanking DNA fragments were transferred into a *S. lividans* strain TK24. Altogether about 20 kb (=kilobase, 1000 bases) were transferred in five fragments into a foreign host. Of these an about 12 kb DNA fragment, pSY15, causes the production of nogalamycin intermediates in *S. lividans*. The recombinant strain obtained was cultivated in a nutrient medium used for anthracycline producers and the product was extracted by suitable organic solvents.

DNA fragments according to the invention were transferred into Streptomyces strains described hereinafter as well as to *S. galilaeus* mutants H028, JH003, H061, H036 and H039 given in Table 2, and expressed in them. Said DNA fragments can correspondingly be transferred to other mutants mentioned in the table, depending on what kind of products are desired.

*Streptomyces lividans* 66, strain TK24, restriction-modification-free strain.

*Streptomyces galilaeus* ATCC 31615, produces aklacinomycin.

Mutants of *Streptomyces galilaeus* ATCC 31615 (cf. Table 2) (Ylihonko et al., 1994).

TABLE 2

The products of *Streptomyces galilaeus* mutants; abbreviations used: Akn = aklavinone, aglycone moiety of aclacinomycins; Rhn = rhodosamine; dF = deoxyfucose, CinA = Cinerulose A; Rho = rhodinose

| Mutant | Product | Description of mutation |
|---|---|---|
| H028 | No production | Mutation in PKS-domain |
| JH003 | No production | Mutation in PKS-domain |
| H061 | 2-OH-Aklanone acid | No removal of 2-OH |
| H036 | Methyl ester of aklanone acid | The fourth ring does not get closed |
| H039 | 1) Aklavinone 2) Akn-Rho-Rho | Amino sugar is missing. |
| H038 | Akn-Rho | Mutation in glycosylation |
| H026 | Akn-Rhn-dF-Rho | Oxidoreductase is missing |
| H035 | Not identified | Mutation in the glycosylation |
| H054 | 1) Akn-Rho-dF-CinA 2) Akn-dF-dF-CinA 3) Akn-Rho-dF-Rho 4) Akn-Rho-dF 5) Akn-dF-dF | Amino sugar is missing |

When producing the starting product for biotransformation the host used is preferably *S. lividans*, because it does not itself produce coloured or extractable compounds in the growth conditions used.

When producing an aglycone for biotransformation the bacterial strains producing anthracyclines or non-producing mutants thereof are preferably used, most preferably non-producing mutants of *S. galilaeus* being transformed with plasmid pSY15 (FIG. 3), carrying the above mentioned 12 kb DNA fragment.

When converting the anthracycline precursors obtained using the plasmid pSY15 to anthracyclines or their aglycones, *S. galilaeus* mutants, e.g. strains JH003 or H028, which do not produce aclarubicin are preferably used.

The DNA-con structions according to th e present invention can be constructed by ligating suitable DNA fragments from the domain as described to a suitable vector. Such a vector is preferably the high copy number plasmid pIJ486 capable to amplify in several strains of the genus Streptomyces (Ward et al., 1986).

To produce anthracyclines and their precursors strains carrying the pSY15 plasmid are grown preferably in growth media for Streptomyces bacteria, preferably in E1-medium, to which thiostrepton has been added to maintain the plasmid carrying strains. The strains are grown in conditions which are advantageous to the producing strain, e.g. in a shaker in bottles, or in a fermenter which is stirred and aerated. After a suitable cultivation time, preferably after 2–7 days the products are isolated according to methods described for bacterial metabolites, preferably e.g. extracting with a suitable solvent, e.g. toluene or chloroform. The extracted compounds are purified with suitable methods e.g. by using column chromatography.

Anthracycline precursors are converted to anthracyclines in strains naturally producing anthracyclines, or mutants thereof. Compounds similar to those naturally produced by the strain are thus obtained, having methyl in their 9-position and hydrogen in their 2-position. In biotransformations auramycinone produced by a *S. galilaeus* strain carrying the plasmid pSY15 is most suitably used as the starting compound, or methyl ester of nogalonic acid produced by a strain carrying the same plasmid which naturally does not produce anthracyclines. In biotransformations most preferably non-producing mutants of anthracycline production strains are used, e.g. mutant H028 or JH003. Biotransformation is effected most preferably by cultivating a strain in a suitable liquid production medium, e.g. in E1-medium, and by adding anthracycline precursors in suitable amounts. After a suitable time, e.g. 6 to 48 hours, most preferably 16 to 32 hours, the anthracyclines so formed are extracted.

The strains used for transformation (cf. also Table 2) are described in the following.

TK24 is a *S. lividans* strain which in the growth conditions used does not produce coloured secondary metabolites. In other growth conditions it produces actinorhodin, which is an antibiotic differing very much from anthracyclines. The strain does not produce any anthracyclines nor their precursors. When characterizing the products of TK24/pSY15 on the basis of NMR-spectrum compound I was obtained as the primary product, which is possibly an intermediate of anthracycline biosynthesis (cf. Scheme I).

H028 is a mutant of *Streptomyces galilaeus* which does not as such produce anthracyclines or their precursors. However, this strain can be used in biotransformations to convert anthracycline precursors to products similar to aclarubicin. When characterizing H028/pSY15 products it was found that this strain produces auramycinone (Compound 11), which is an anthracycline aglycone similar to aklavinone, as well as auramycins which are glycosides of auramycinone, e.g. Compound III. When hydrolyzing auramycins auramycinone is obtained, which also shows that the compounds produced are glycosides of auramycinone. Auramycinone is a useful precursor of anthracyclines, when new anthracyclines are produced by biotransformation. Auramycins have been described to be cytostatic anthracyclines having possible use in cancer chemotherapy. The use of H028/pSY15 for the production of these is new.

H061 is a *Streptomyces galilaeus* mutant, which produces 2-OH-aklanone acid. This is evidently due to a mutation which prevents removal of the hydroxyl in 2-position. H061/pSY15 produces aklavinone, auramycinone and their glycosides similar to aclarubicin. According to the result pSY15 complements the mutation of H061 and comprises thus the gene encoding the 2-position dehydroxylase. This is useful in producing new hybrid compounds when transformed to a strain the products of which naturally have hydroxyl or a methoxy group in 2-position.

On the basis of the results pSY15 is useful in producing precursors of anthracyclines in strains which naturally do not produce anthracyclines, or when producing hybrid anthracyclines in strains which produce anthracyclines, or in mutants thereof. With it the formation of 9-position side chain can be affected so that the strains which provide a two carbon side chain at this position, do produce compounds which have a one carbon side chain at said position. Possible strains producing anthracyclines which can be modified this way are e.g. *S. galilaeus*, *S. peucetius* and *S. purpurascens*. The anthracycline precursors produced this way are useful in producing new anthracyclines by biotransformations. pSY15 can also be transferred to a strain which normally produces compounds which at 2-position have hydroxyl or a methoxy group. Thereby compounds are obtained which have hydrogen at this position. pSY15 enables also one to produce previously described auramycinone and its glycosides by the new method.

In the following the detailed embodiments of the invention are described as examples of isolation of the DNA fragment from *S. nogalater* strain ATCC 27451, production of nogalamycin precursors in *S. lividans* strain TK24, production of auramycinone in the mutant H028 and their modification to anthracyclines in the mutant JH003. In addition, expression of the DNA fragments according to the invention in the mutants of the strain *S. galilaeus* is described, as well as the compounds produced by these strains.

The main products of the strains TK24/pSY15, H028/pSY15, H028/pSY15 and H061/pSY15 were characterized.

BRIEF DESCRIPTION OF DRAWINGS

FIG. 1A Anthracyclines produced by Streptomyces strains, and identified precursors thereof. (Starting molecule: propionate.) The numbers of *S. galilaeus* mutant strains producing the intermediates are given in parentheses.

DESCRIPTION OF EXAMPLORY EMBODIMENT

Bacterial strains and plasmids

Figure 1B:
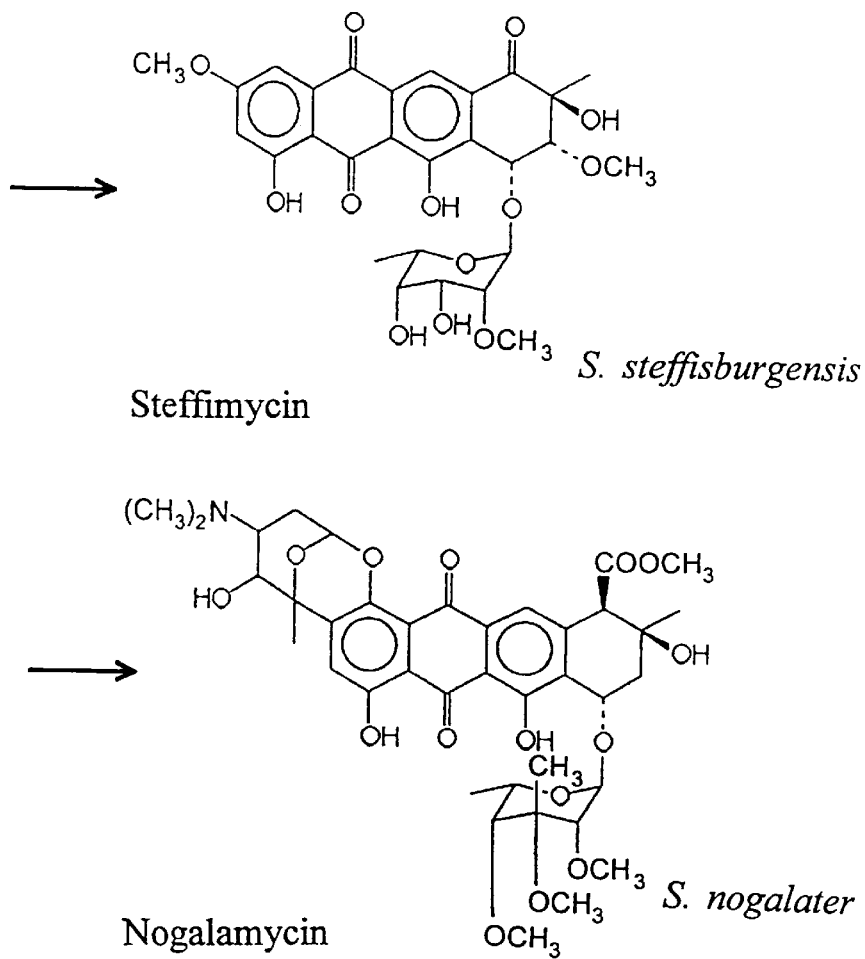
FIG. 1B Anthracyclines produced by Streptomyces strains having acetate as the starting molecule.

The strain *Streptomyces nogalater* ATCC 27451 was used as the donor of genes. The Streptomyces bacterial strains used in this work as hosts are listed above. The treatments of *S. nogalater* DNA were effected in the *E. coli* strain XL1-Blue (recA1, endA1, gyrA96, thi-1, hsdR17, supE44, relA1, lac, [F'proAB, lacIZΔM15, TnIO (tet$^r$)] (Stratagene Cloning Systems, California). *E. coli* strains GM2163 (*E. coli* Genetic Stock Center, Department of Biology 255 OML, Yale University, New Haven, USA) and LE392 (Promega) were used in preparing the gene bank and in amplifying the phage DNA.

In *E. coli* the plasmids pUC18/pUC19 (Pharmacia Biotech) were used, and in Streptomyces strains the plasmid pIj486 was used (Ward et al., 1987; obtained from Prof. Hopwood, John Innes Centre, UK).

Nutrient media and solutions used

TRYPTONE-SOYA BROTH (TSB)
Per litre: Oxoid Tryptone Soya Broth powder 30 g.
YEME (Hopwood et al., 1985., p. 239)
Per litre: Yeast extract (Difco) 3 g, Bacto-peptone (Difco) 5 g, malt extract (Oxoid) 3 g, glucose 10 g and saccharose 340 g. After autoclaving 2 ml of sterile 25M MgCl$_2$ solution and 25 ml of 20% glycine are added.

SGYEME As YEME, but the amount of saccharose was 110 g per litre. To prepare protoplasts the amount of 20% glycine varies from 12 ml to 50 ml per litre depending on the strain used.

YM-agar Bacto Yeast malt extract agar, ISP-medium 2, Difco; 38 g/litre.

ISP4 Bacto ISP-medium 4, Difco; 37 g/litre.
R2YE Hopwood et al., (1985 p. 236)
LB Sambrook et al., (1989, 3:A1)
E1 Per litre: Glucose 20 g, starch 20 g, Farmamedia 5 g, yeast extract 2.5 g, K$_2$HPO$_4$. 3H$_2$O 1.3 g, MgSO$_4$. 7H$_2$O 1 g, NaCl 3 g, CaCO₃ 3 g. Tap water is added to 1 litre and pH is adjusted to 7.4.

TE Tris-HCl-buffer, pH 8: 10 mM, EDTA, pH 8: 1 mM
20×SSC Per litre: NaCl 175.3 g, Na-citrate 88.2 g. pH is adjusted to 7 with NaOH.

DENHARDT SOLUTION (Sambrook et al., 1989, 3:B.1)

A 50× basic solution is prepared, which contains Ficoll 5 g, polyvinyl pyrrolidone 5 g, BSA (bovine serum albumin) 5 g. Distilled water is added to 500 ml and sterilized by filtrating.

EXAMPLE 1

Cloning and Characterization of the Genes Included in the Anthracycline Biosynthesis of *Streptomyces nogalater*

1.1 Preparing of gene bank and cloning of anthracycline genes from *S. nogalater*.

Isolation of the total DNA from *Streptomyces nogalater*

*S. nogalater* (ATCC 27451) mycelia were cultivated for about 3 days in 50 ml of TSB medium, wherein 0.5% glycine had been added at 28° C. vigorously shaking. The mycelia were pelleted and the supernatant was discarded. The pellet was suspended into 10 ml of lysis buffer (15% saccharose, 25 mM Tris, pH 8.0, 25 mM EDTA and 5 mg/ml of lysozyme) and incubated for 15 min at 37° C. 1 mg of proteinase K and 1 ml of 10% SDS were added while stirring. The mixture was incubated at once for 15 min at 70° C. The lysed pellet was subsequently cooled in ice, 1 ml of 3 M Naacetate (pH 6.0) was added and kept for a few minutes on ice bath. 5 ml of phenol balanced with 0.1 M Tris was added and stirred by turning the tube around. The phases were sentrifuged apart and the water phase was further extracted with 5 ml of chloroform. DNA was subsequently precipitated by adding 10 ml of isopropanol. DNA was spinned cautiously around a Pasteur pipette being closed by flaming, washed by dipping into 70% ethanol and DNA was loosened onto the wall of the tube. DNA was dissolved in 5 ml of TE-buffer and treated with RNase (25 µl of 10 mg/ml DNase free RNase) for about 30 min at 37° C. The phenol and chloroform extractions were repeated. DNA was subsequently reprecipitated with isopropanol and washed as above. Finally DNA was dissolved in 1 ml of TE-buffer and it was used for subsequent steps.

Southern hybridization

The actI probe was the 0.8 kb BglII-fragment obtained from the plasmid pIj2345 and the acm probe the 3 kb BamHI-fragment obtained from the plasmid pACM5 (Niemi et al., 1994). The plasmids were isolated at mini-scale (Magic Minipreps reagent series of Promega) and the probe fragments were isolated by preparative agarose gel electrophoresis after digesting them first with BglII and with BamHI, respectively. The probes were then labeled with 50 µCi of [α³²-P]CTP by nick-translation (Nick translation labeling reagent series of Boehringer Mannheim).

The total DNA preparations isolated as described above were digested with EcoRI enzyme and fractionated with agarose gel electrophoresis. The fractionated DNA was transferred from the gel to Hybond N membrane (Amersham) using the Vacugene apparatus (LKB 2016, Pharmacia LKB Biotechnology) according to the instructions of use. DNA was fastened into the membrane by incubating for 3 min in UV light.

The membranes were hybridized in 10 ml of hybridization solution (1% SDS, 1M NaCl, 5× Denhardt's solution, 100 µg/ml denatured carrier DNA (DNA from calf thymus, Boehringer Mannheim) at 65° C. in a hybridization oven (HB-1D Hybridiser, Techne) for about 6 h, whereafter at least 100 ng of labeled probe-DNA was added into the hybridization tube and the incubation was continued for further about 12 h. After this the membranes were washed at 65° C. for 2×30 min in a wash solution (2×SSC, 1% SDS or 0.2×SSC, 0.1% SDS). Autoradiography was effected by superimposing the membrane coated with a plastic film and the autoradiography film. Exposure lasted about 1 to 3 days.

Preparing of the gene bank from *S. nogalater* DNA

40 µg of DNA was incubated in the digestion buffer (10×A, Boehringer Marnnheim) in the presence of 2.4 units of Sau3A (Boehringer Mannheim) for 5 min at 37° C. and the reaction was stopped by adding phenol. After phenol treatment DNA was purified with ethanol precipitation. DNA-fragments so obtained were run at preparative agarose gel electrophoresis (0.3% LGT, low gelling temperature). DNA, which was 20 kb or bigger, was taken from the gel by cutting and purified by phenolization from the agarose. A commercial phage vector, λ EMBL 4, BamHI fragments (Amersham International plc, Amersham UK) were treated with alkaline phosphatase (CIAP, calf intestinal alkaline phosphatase, Promega) according to the instructions of the manufacturer. The insert DNA (Sau3A fraction) and vector so obtained were ligated by incubating for 2 h at room temperature and for 2 h at 14° C. in the presence of T4-DNA ligase (Promega) according to the recommendation of the manufacturer. The ligation mixture was packed to λ-particles using the Packagene reagent series (Promega Biotech) according to the manufacturer's instructions. *Escherichia coli* strain GM2163 was used as the host. The cells were prepared for infection according to the packing instructions and cells infected with the packing mixture were spread onto plates according to Promega's instructions.

Isolation and mapping of hybridizing clones

Phage DNA from plates with about 4000 plaques/plate was transferred to a membrane (Colony/Plaque Screen, New England Nuclear) according to the manufacturer's instructions. The membranes were hybridized as described above. Plaques which gave a signal in autoradiography, were picked up and the phages were eluted from them by incubating a plaque in 0.5 ml of SM-buffer for 2 hours. Because the plaque plates were dense, the plaques were purified by infecting them into the host strain LE392 (Promega) and hybridizing as above.

Figure 2:
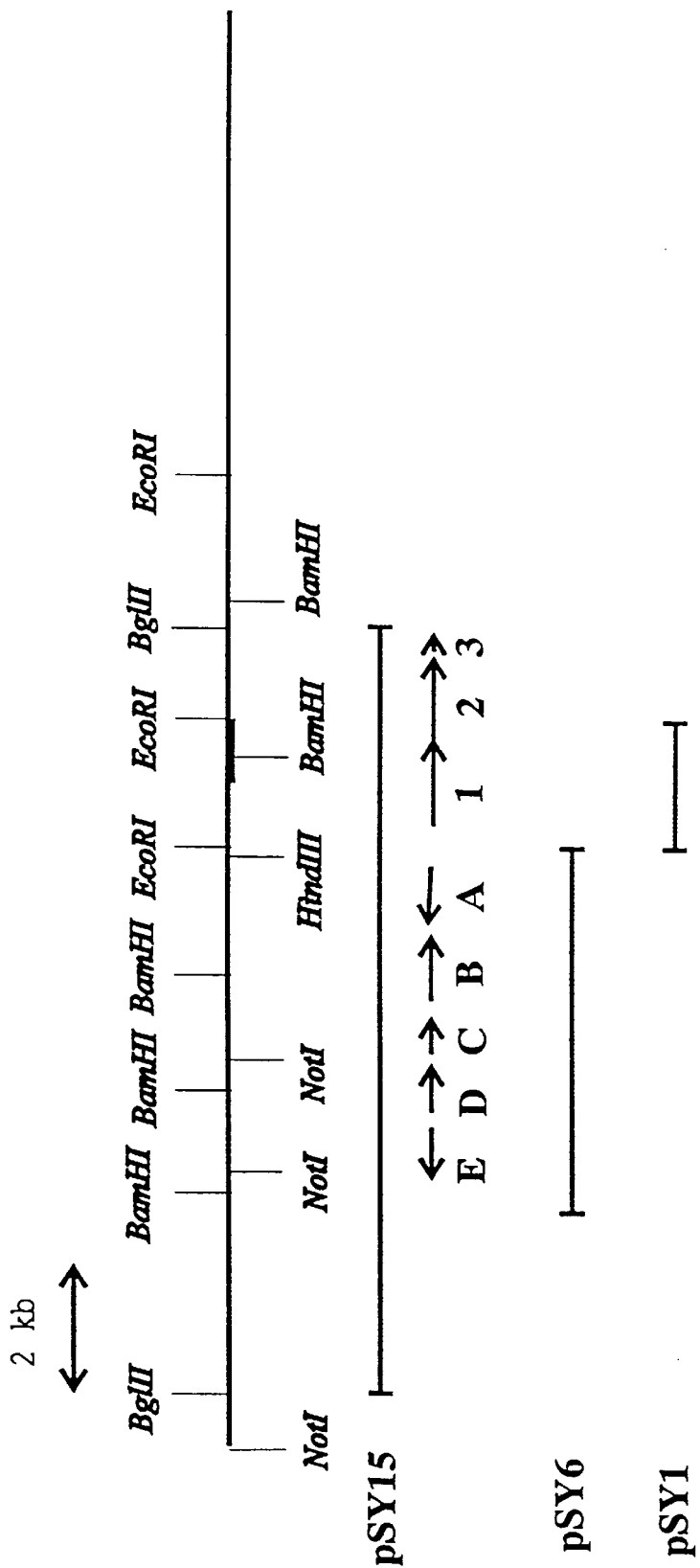
FIG. 2 Restriction map of the 12 kb continuous DNA fragment cloned from *S. nogalater* genome. The figure discloses also the inserts contained in the pSY plasmids obtained. Plasmid pIJ486 has been used in preparing the pSY vectors. On the basis of sequence comparisons the following functions have been obtained for the open reading frames shown in the figure: 1=ketoacylsynthase-acyltransferase, 2=Chain Length Controlling Factor (CLF), 3=acyl transferring protein; A and B=regulatory genes, C=mono-oxygenase, D=methyl transferase, E=ketoreductase.
Figure 3:
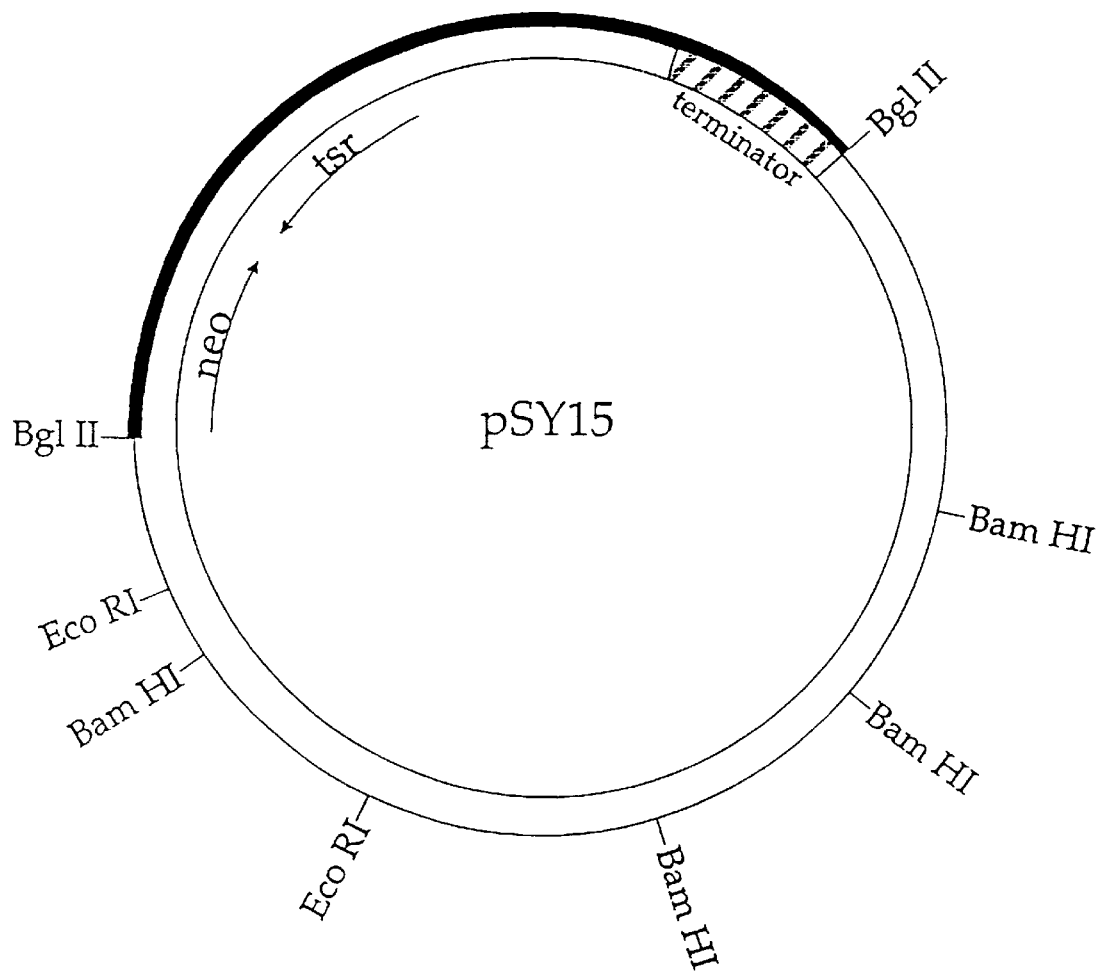
FIG. 3 Structure of the plasmid pSY15.

From the purified clones phage DNA was prepared in 20 ml scale by infecting the LE392 cells according to Promega's packing instructions. The DNA so obtained was digested with various restriction endonucleases to map the clones (Sambrook et al., 1989) and by hybridizing with different probes. The restriction map so obtained is given in FIG. 2.

Transfer of the DNA fragments to *S. lividans* and detection of new compounds

The fragment shown in the restriction map (FIG. 2) was transferred into *S. lividans* as EcoRI-fragments (pSY1 and pSY6) or as a BglII-fragment (pSY15). λ-clones were digested with EcoRI or BglII-restriction enzyme and ligated to a plasmid made linear with the same enzyme and was transformed by electroporation into *E. coli* or by protoplast transformation into *S. lividans*. Most of the inserts were first cloned into the plasmid pUC19 amplifying in *E. coli*, whereby as a host *E. coli* strain XL1-Blue was used. pSY15 was cloned directly into the *S. lividans* strain TK24. *E. coli* was used because by that way smaller amounts of phage-DNA could be used. The transformation efficacy of *E. coli* was 2×10⁸ transformants/µg DNA, when *E. coli* Pulser Apparatus-electroporation device (Bio-Rad) was used with the following settings (200 Ohm, 25 µF, 1.4 kV). For electroporation the cells were treated as described in Dower, W. J. et al. (1988), and 0.1 cm cuvettes of Bio-Rad were used in transformation, the cell volume was 20 μl.

S. lividans strain TK24 was used as an intermediate host as the expression was believed to be successful only in S. galilaeus strains. S. galilaeus is not at all transformable with DNA propagated in E. coli. Only the plasmid pSY15 caused modification in TK24 strain, which was noticed as brown colour on the ISP4 plate, when TK24 is normally rather colourless or blue. Only the TK24 strain carrying the plasmid pSY15 caused formation of coloured products in the E1-medium well suited for the production of anthracyclines. On the basis of thin layer chromatography the products of the recombinant strain TK24/pSY15 seemed to be alike to but not identical with those produced by the mutant H036 (Ylihonko et aL, 1994) producing the methyl ester of aklanone acid. With the eluent toluene:ethyl acetate:methanol:formic acid (50:50:15:3) the following $R_f$-values were obtained for these products:

TK24/pSY15: 0.66; 0.60; 0.50

H036: 0.67; 0.62; 0.51.

These characteristics were confirmed to come from the pSY15 plasmid by retransforming the plasmid to S. lividans TK24 strain. The transformants so obtained were also able to produce anthracycline precursors. When the recombinant strain was cultivated in E1 medium without selection pressure of the plasmid strain caused by thiostrepton, the production of new compounds decreased.

1.2 Localizing the PKS-genes

Sequencing of the hybridizing fragment

From the EcoRI-digest a 2 kb actI hybridizing fragment was obtained and it was sequenced. About 2 kb of DNA to the right according to the map (FIG. 2) was additionally sequenced. For sequencing 31 clones were prepared from restriction enzyme digestion sites to the vectors pUC18 and pUC19, being linearized with corresponding enzymes.

To isolate plasmids for the sequencing reactions Magic/Wizard™ Minipreps DNA Purification System kit of Promega was used. E. coli XL1-Blue cells were cultivated overnight in 3 ml of LB-medium which contained 50 μg/ml of ampicillin, and the plasmids were isolated according to the manufacturer's instructions.

DNA-sequencing was performed by using dideoxy chain termination method. For the sequencing reactions Deaza G/A $^{T7}$Sequencing™ Mixes (Pharnacia) and TaqTrack® Sequencing Systems, Deaza (Promega) sequencing reagent series were used. Denaturation was always performed according to the instructions in the Pharmacia kit. (Method C). When using the Pharmacia kit the primers were ligated according to the Method C given in the instructions (Standard Annealing of Primer to Double-Stranded Template). When using the Promega kit the item "Sequencing Protocol Using Direct Incorporation" of the manufacturer's instructions was followed. Deviating from the primer ligation temperature (37° C.) recommended by the manufacturer the temperature of 45° C. was used to avoid the secondary structures caused by the high GC-content. The temperature was kept thereafter at 45° C. until the end of the reaction. As a radioactive label [$\alpha^{35}$S]dATP (NEN Products Boston, Mass.) was used. Most of the PKS-domain was sequenced with a universal primer (5'-d(GTTTTCCCAGTCAC-GAC)-3') SEQ ID NO:6 and with a reverse primer (5'-d(CAGGAAACAGCTATGAC)-3' SEQ ID NO:7 (pUC/M13 17' mer Primers, Promega). When sequencing the longest fragments (500–600 bp) of the domain, and in order to define the sequences of such restriction sites which could not be "passed", six specific primers were used. The primers were prepared at the Department of Bioorganic Chemistry in the University of Turku.

The sequencing gels were run by the Macrophor-system of Pharmacia, using a 4% thickness gradient gel. Running conditions: current 20 mA, voltage 2500 V.

Sequence analysis

From the PKS domain the DNA fragment with about 4134 bases (as given in the sequence listing) was sequenced, the analysis of which was performed by GCG-software (Genetics Computer Group, GCG Package, Wisconsin USA). With the subprogram CODONPREFERENCE the open reading frames were sought from the sequence. The reading frames obtained were translated to the amino acid sequence and with the TFASTA-subprogram homologies to known sequences were sought.

According to the CODONPREFERENCE program the 4134 base DNA fragment as sequenced had altogether three open reading frames (ORF1, ORF2, ORF3) (ORF 1 is the fragment 359–1651 in SEQ ID NO:1 of the sequence listing, ORF2 is the fragment 1648–2877 in the SEQ ID NO:4, and ORF3 is the fragment 2937–3197 in the SEQ ID NO:1). In the beginning of each open reading frame a possible ribosome binding site was found (RBS). The functions of the genes were concluded by comparing the amino acid sequences translated from their base sequences to known sequences. So the following similarities with the open reading frames of actinorhodin and tetracenomycin PKS domains were obtained: ORF1 (80%, 81%), ORF2 (74%, 77%), ORF3 (62%, 62%), and on the basis of this we present the following functions to said genes: ORF1 is ketoacylsynthase; ORF2 is the factor which effects on the chain length; ORF3 is an acyl carrier protein. These three open reading frames are needed for a functional polyketide synthase.

Upstream of the PKS domain about 6 kb DNA fragment was sequenced (kb=1000 bases). In this domain the following gene activities have been recognized on the basis of the sequence: (FIG. 2): regulatory genes, mono-oxygenase, methyl transferase and ketoreductase.

EXAMPLE 2

Transfer of the Genes into the Strain S. galilaeus ATCC 31615 and Mutants Thereof Plasmid pSY15 was isolated from S. lividans strain TK24 and transformed into S. galilaeus mutant H039 and the DNA isolated therefrom further into other S. galilaeus mutants. The method used in the transformation of the S. galilaeus strain being modified from the transformation method used in the transformation of S. lividans has been described earlier (Ylihonko, K, Pro gradu-thesis, University of Turku, 1986). For preparing protoplasts the cells were grown in SGYEME, to which 0.8% saccharose had been added. The plasmids were transformed successfully first to the mutant H039, whereby with 2 μg of plasmid-DNA about 10 transformants were obtained. Because of a strong restriction barrier S. galilaeus is weakly transformable with foreign DNA but the transformation efficacy increases manyfold if the plasmid has been isolated from a S. galilaeus strain.

H039-transformants were first cultivated for about 5 days on an ISP4 plate, whereto thiostreptone had been added. The mycelium was inoculated in 50 ml of TSB nutrient broth (5 μg/ml of thiostreptone added) and grown in a shaker for 5 days. The plasmid was isolated as described above and transformed into other mutants. Usually 200 to 500 ng of plasmid was used per one transformation, whereby 10 to 100 transformants were obtained.

After regeneration the transformed mutant strains were spread onto ISP4 plates, wherefrom the mycelium was further transferred to E1 nutrient medium. To retain the plasmid thiostrepton was added to all nutrient media. E1 mycelium was incubated in a shaker (330 rpm, 30° C.) and production was followed by taking after 3 days a 0.5 ml sample of the mycelium daily for 3 to 5 days. The sample was buffered to pH 7 with phosphate buffer and extracted with methanol-toluene mixture (1:1). In addition, part of the samples were acidified with 1M HCl solution and extracted into toluenemethanol. In E1-cultivations both mutants and the *S. galilaeus* wild strain were used as controls. By comparing the products on TLC the effects of the plasmid on the production were seen.

The *S. galilaeus* mutants used in transformations are listed above. Plasmid pSY15 complemented, i.e. restored the producing ability of anthracyclines or precursors thereof in the following mutants: H028, H061 and JH003. It did not affect the production profile of the mutants H036 and H039 to any appreciable extent. JH003, which does not produce coloured compounds in the conditions used, has been mutated from the strain H054 and the transformant JH003/pSY15 was compared to the strain H054. H028 is also a non-producing mutant, which was obtained by mutating the wild strain *S. galilaeus* ATCC 31615. So the wild strain was used as the control of the transformant H028/pSY15. Using the eluent toluene:ethyl acetate:methanol:formic acid (50:50:15:3) the following $R_f$-values were obtained for the transformants and the host strains used as controls.

H028/pSY15: (0.69); 0.61; 0.58; 0.01

JH003/pSY15: 059; 0.50; 0.46; 035

H061/pSY15: (0.69); 0.61; 0.58; 0.06; 0.01

*S. galilaeus* ATCC 31615: 0.23; 0.14; 0.11

H054: 0.65; 0.60; 0.53; 0.48.

H061: 050 (acid).

The product isolated in small scale was hydrolyzed by heating in 1M hydrochloric acid at 80° C. for 0.5 h. After hydrolysis the following $R_f$-values were obtained for the aglycons or precursors thereof:

H028/pSY15: 0.61

JH003/pSY15: 0.61

H061/pSY15: 0.61.

Because all these mutants used have originally been produced from a *S. galilaeus* wild strain, aklavinone was used as comparison, being the aglycone of aclacinomycins produced by *S. galilaeus*. In the eluent used the $R_f$-value 0.69 was obtained for aklavinone. In the products of transformants small amounts of aklavinone were also detected.

EXAMPLE 3

Production of Anthracycline Precursors 3.1 Production of TK24/pSY15 products

Ten 250 ml erlenmeyer-flasks each containing 60 ml of E1-medium were inoculated with 1 ml aliquots of the strain TK24/pSY15. The flasks were incubated in a shaker at 330 rpm at the temperature of 30° C. for about 3 days. From the finished mycelia production was confirmed by extracting 0.5 ml samples with a mixture of methanol and toluene (1:1). The products were compared to the standard by thin layer chromatography.

The flasks were emptied into two 400 ml centrifuge tubes and centrifuged for 10 min at 3000 rpm. The supernatant was recovered. The precipitate was suspended by adding to each tube 50 ml of methanol. The tubes were recentrifuged for 10 min at 3000 rpm. The methanol solution was added into the supernatant. The precipitate was discarded. The solution was extracted with 2×100 ml of chloroform, whereby a strongly orange-yellow chloroform solution was obtained. The water phase was discarded.

Chloroform was evaporated on a water bath in a rotary evaporator. The orangeyellow, dry product was dissolved in 2 ml of chloroform.

The chloroform solutions were pipetted into a chromatography column of glass, equipped with a glass sinter, having a diameter of 2 cm and containing about 5 cm of silica suspended in chloroform (Kieselgel 60, Merck). The column was eluted with 2.5 ml aliquots of chloroform. Each fraction was collected into a separate test tube. Samples of each fraction were dropped on a thin layer and compared to the standards. Fractions containing individual compounds were pooled and evaporated into dryness.

Figure 4:
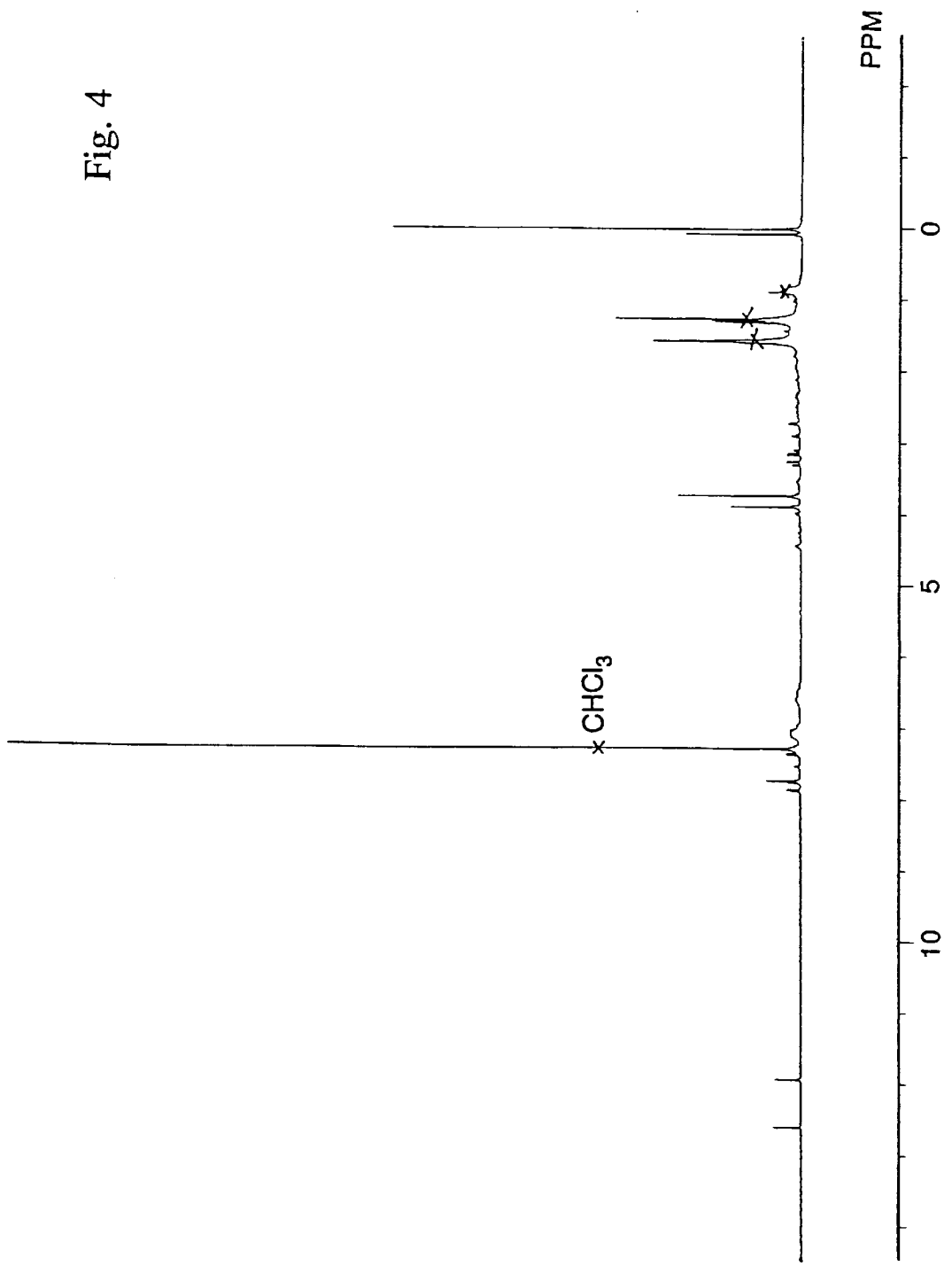
FIG. 4 NMR-spectrum of compound I.

NMR-spectra of pure compounds were determined and the compounds were identified by comparing the spectra with analogical compounds. In FIG. 4 the H-NMR-spectrum of Compound I is given.

3.2 Production of an aglycone in the strain H028/pSY15

Ten 250 ml erlenmeyer-flasks each containing 60 ml of E1-medium were inoculated with 1 ml aliquots of the strain H028/pSY15. The flasks were incubated in a shaker at 330 rpm at the temperature of 30° C. for about 4 days. From the finished mycelia production was confirmed by extracting 0.5 ml samples with a mixture of methanol and toluene (1:1). The products were compared to the standards by thin layer chromatography.

The flasks were emptied into two 400 ml centrifuge tubes and centrifuged for 10 min at 3000 rpm. The supernatant was recovered. The precipitate was suspended by adding to each tube 50 ml of methanol. The tubes were recentrifuged for 10 min at 3000 rpm. The methanol solution was added into the supernatant. The precipitate was discarded. The solution was extracted with 2×100 ml of chloroform, whereby a strongly yellow chloroform solution was obtained. The water phase was discarded.

Chloroform was evaporated on a water bath in a rotary evaporator. The yellow, dry product was dissolved in 2 ml of chloroform.

The chloroform solutions were pipetted into a chromatography column of glass, equipped with a glass sinter, having a diameter of 2 cm and containing about 5 cm of silica suspended in chloroform (Kieselgel 60, Merck). The column was eluted with 2.5 ml aliquots of chloroform. Each fraction was collected into a separate test tube. Samples of each fraction were dropped on a thin layer and compared to the standards. Fractions containing individual compounds were pooled and evaporated into dryness.

Figure 5:
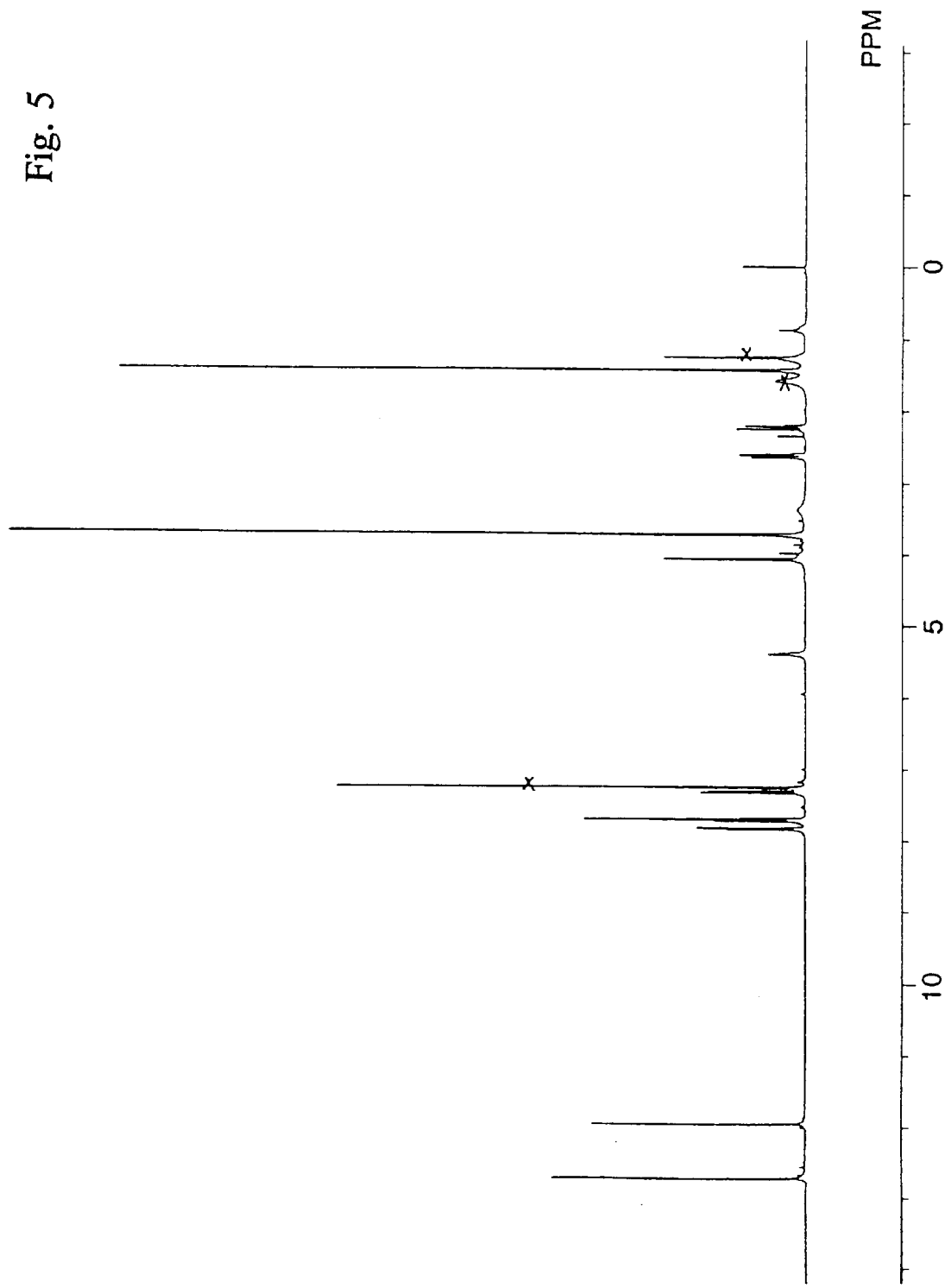
FIG. 5 NMR-spectrum of auramycinone.

NMR-spectra of pure compounds were determined and the compounds were identified by comparing the spectra with analogical compounds. In FIG. 5 the H-NMR-spectrum of auramycinone (Compound II) is given.

EXAMPLE 4

Biotransformation of Hybrid Products 4.1 Biotransformation of auramycinone in strain JH003

A 250 ml erlenmeyer-flask containing 60 ml of E1-medium was inoculated with 1 ml of strain JH003. The flask was incubated in a shaker at 330 rpm at the temperature of 30° C. for about 3 days. After two day's cultivation about 2 mg of auramycinone was added into the flask. At 24 hours from this the production was confirmed by extracting a 0.5 ml sample with the mixture of methanol and toluene (1:1). The products were compared to the standard by thin layer chromatography.

The flask was emptied into two 60 ml centrifuge tube and centrifuged for 10 min at 3000 rpm. The supernatant was recovered. The precipitate was suspended by adding to each tube 10 ml of methanol. The tubes were recentrifuged for 10 min at 3000 rpm. The methanol solution was added to the supernatant. The precipitate was discarded. The pooled solution was extracted with 2×20 ml of chloroform, whereby a strongly yellow chloroform solution was obtained. The water phase was discarded.

Chloroform was evaporated on a water bath in a rotary evaporator. The yellow, dry product was dissolved in chloroform. On the basis of TLC the product was found to correspond to the products of the strain JH003/pSY15 (cf. Example 5.2).

EXAMPLE 5

Production of Hybrid Anthracyclines 5.1 Production of auramycinone-rhodosamine-deoxyfucose in strain H028/pSY15

Ten 250 ml erlenmeyer-flasks each containing 60 ml of E1-medium were inoculated with 1 ml aliquots of the strain H028/pSY15. The flasks were incubated in a shaker at 330 rpm at the temperature of 30° C. for about 4 days. From the finished mycelia production was confirmed by extracting 0.5 ml samples with a mixture of methanol and toluene (1:1). The products were compared to the standard by thin layer chromatography.

The flasks were emptied into two 400 ml centrifuge tubes and centrifuged for 10 min at 3000 rpm. The supernatant was recovered. The precipitate was suspended by adding to each tube 50 ml of methanol. The tubes were recentrifuged for 10 min at 3000 rpm. The methanol solution was added into the supernatant. The precipitate was discarded. The pooled solution was extracted with 2×100 ml of chloroform, whereby a strongly yellow chloroform solution was obtained. The water phase was discarded.

Chloroform was evaporated on a water bath in a rotary evaporator. The yellow, dry product was dissolved in 2 ml of chloroform.

The chloroform solutions were pipetted into a chromatography column of glass, equipped with a glass sinter, having a diameter of 2 cm and containing about 5 cm of silica suspended in chloroform (Kieselgel 60, Merck). The column was eluted with 2.5 ml aliquots of chloroform. Each fraction was collected into a separate test tube. Samples of each fraction were dropped on a thin layer and compared to the standards. Fractions containing individual compounds were pooled.

Figure 6:
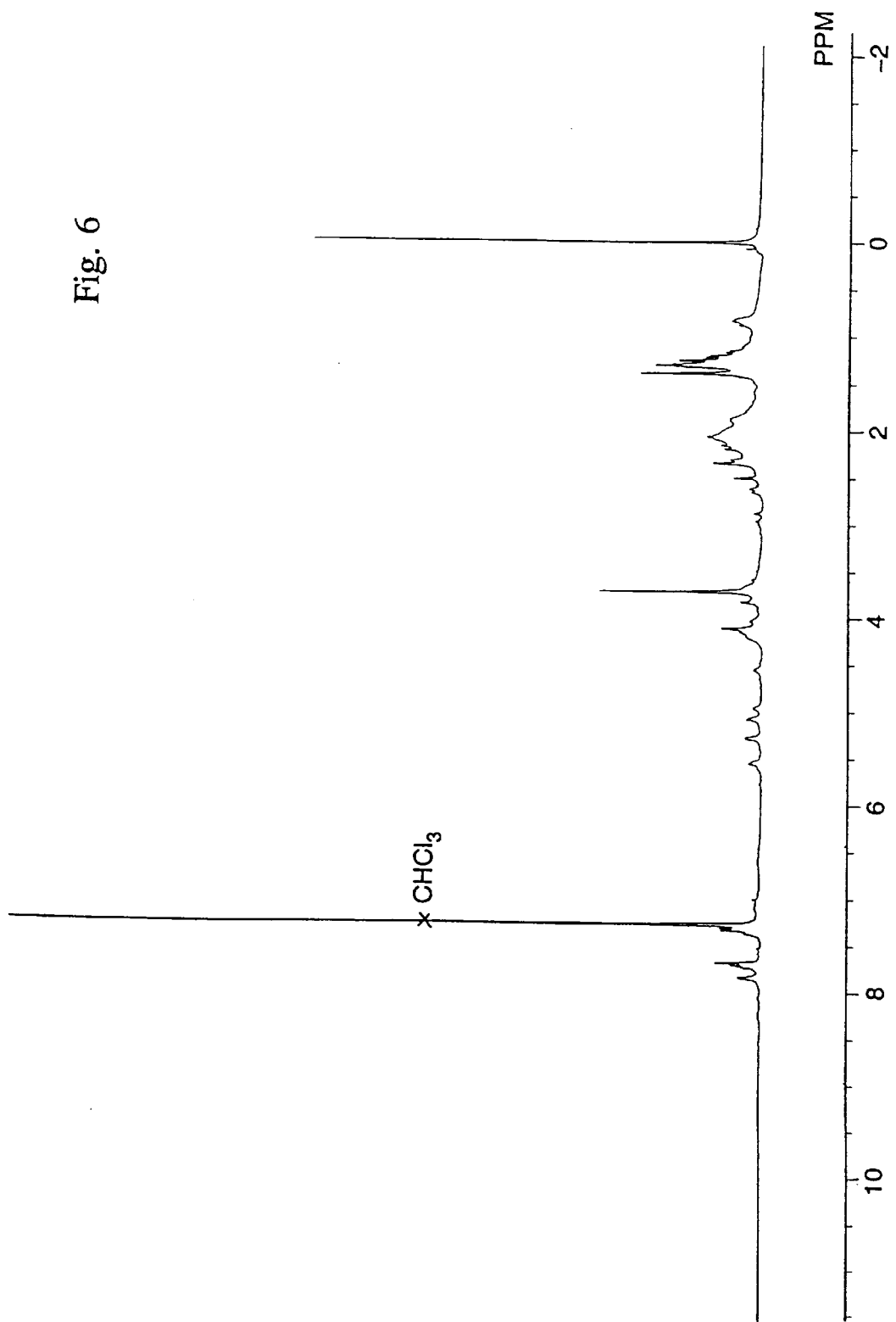
FIG. 6 NMR-spectrum of auramycinone-rhodosamine-deoxyfucose.

NMR-spectra of pure compounds were determined and the compounds were identified by comparing the spectra with analogical compounds. In FIG. 6 the H-NMR-spectrum of auramycinone-rhodosamine-deoxyfucose (Compound III) is given.

5.2 Production of auramycinone-rhodinose-deoxyfucose in strain JH003/pSY15

Ten 250 ml erlenmeyer-flasks each containing 60 ml of E1-medium were inoculated with 1 ml aliquots of the strain JH003/pSY15. The flasks were incubated in a shaker at 330 rpm at the temperature of 30° C. for about 4 days. From the finished mycelia production was confirmed by extracting 0.5 ml samples with a mixture of methanol and toluene (1:1). The products were compared to the standard by thin layer chromatography.

The flasks were emptied into two 400 ml centrifuge tubes and centrifuged for 10 min at 3000 rpm. The supernatant was recovered. The precipitate was suspended by adding to each tube 50 ml of methanol. The tubes were recentrifuged for 10 min at 3000 rpm. The methanol solution was added into the supernatant. The precipitate was discarded. The pooled solution was extracted with 2×100 ml of chloroform, whereby a strongly yellow chloroform solution was obtained. The water phase was discarded.

Chloroform was evaporated on a water bath in a rotary evaporator. The yellow, dry product was dissolved in 2 ml of chloroform.

The chloroform solutions were pipetted into a chromatography column of glass, equipped with a glass sinter, having a diameter of 2 cm and containing about 5 cm of silica suspended in chloroform (Kieselgel 60, Merck). The column was eluted with 2.5 ml aliquots of chloroform:methanol 100:10. Each fraction was collected into a separate test tube. Samples of each fraction were dropped on a thin layer and compared to a standard. Fractions containing individual compounds were pooled and evaporated into dryness.

Figure 7:
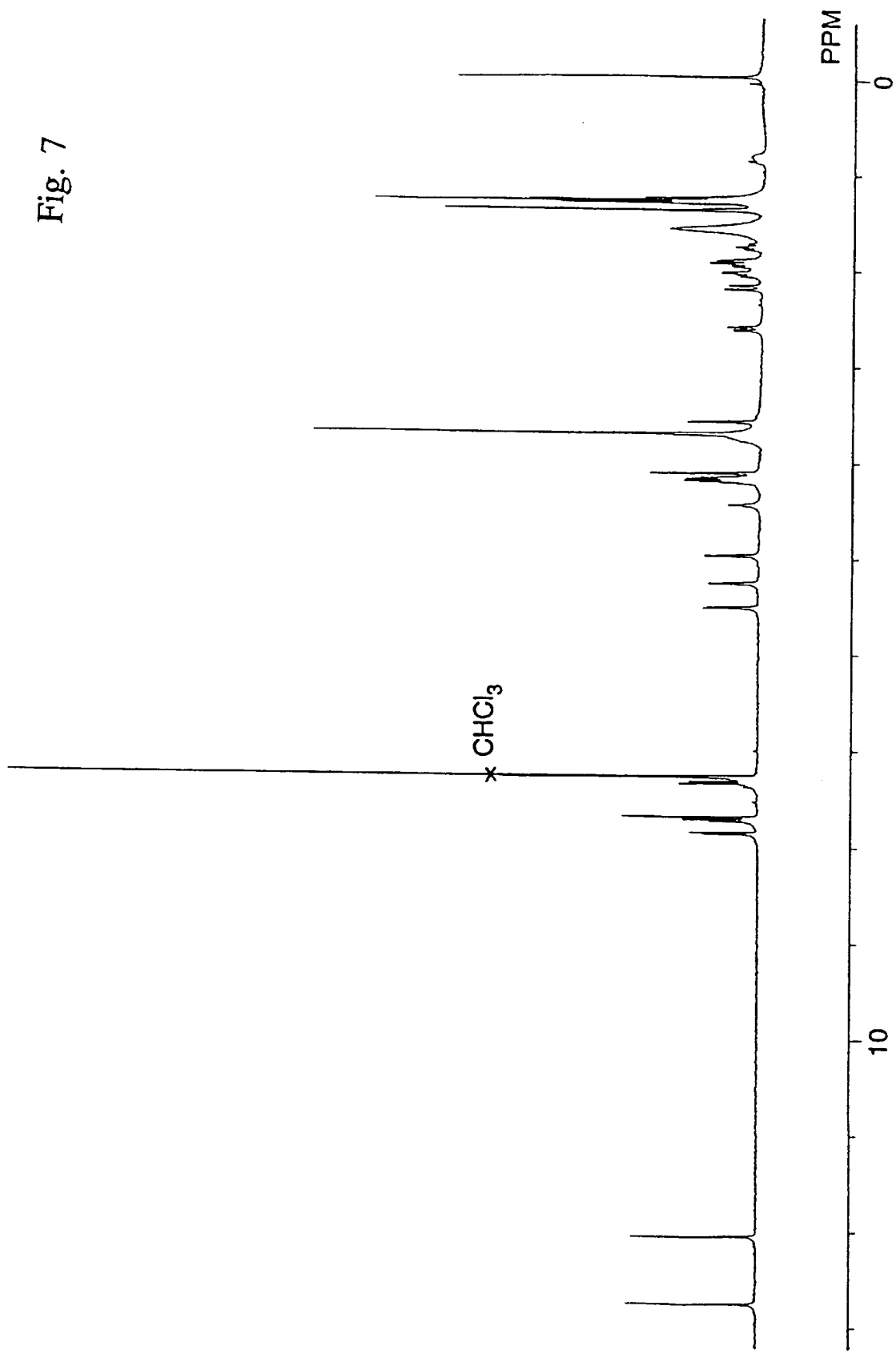
FIG. 7 NMR-spectrum of auramycinone-rhodinose-deoxyfucose.

NMR-spectra of pure compounds were determined and the compounds were identified by comparing the spectra with analogical compounds. In FIG. 7 the H-NMR-spectrum of auramycinone-rhodinose-deoxyfucose is given.

EXAMPLE 6

Characterization of the Products 6.1 HPLC-runs

The retention times of the compounds were determined at RP-18-column, with an eluent acetonitrile:methanol:potassium dihydrogen phosphate buffer (8.00 g/l, pH 3.0) 5:2:3. The retention times of the compounds are: I: 4.63, II: 3.52, III: 4.09 and IV: 7.26. The structures of the compounds I–IV are given in the Scheme I.

6.2 NMR-spectra of the compounds

H-NMR-spectra of some of the TK24/pSY15, H028/pSY15 and JH003/pSY15 products were determined by Brüker 400 MHz NMR spectrometer in deuterium-chloroform. The spectra given by the compounds were compared to the spectra of known compounds, e.g. aclarubicin. The spectra obtained are given in FIGS. 4 to 7.

In all of the compounds the hydrogens in 1, 2 and 3-positions bound to each other and with same transitions are found. The singlet corresponding to the hydrogen in 11-position was found in all compounds with the same transition. Additionally, the peaks given by the two aromatic hydroxyls can be seen. On the basis of the peaks of these six hydrogens the aromatic chromophore moieties are similar, and correspond e.g. the chromophore of aklavinone.

In all of the compounds a singlet of the size of three hydrogens is found at about 3.7 ppm corresponding to the methyl of methyl ester. Another singlet is found in all compounds at about 3.8 ppm, which corresponds to the 10-position hydrogen. The integral of this is of the size of one hydrogen in auramycinone and its glycosides and of the size of two hydrogens in Compound I. According to this Compound I suits to be a compound in which the fourth ring has not been closed.

The region 4.7 to 6 ppm has in anthracyclines and in compounds related thereto hydrogens at 7-position and 1-position of the sugars. Auramycinone has in this region one peak, Compounds III and IV have three peaks, but in Compound I there are no peaks in this region. According to this auramycinone has no sugars and Compounds III and IV have two sugars, whereas Compound I has no hydrogens in this region which suits with the keto-form at position 7.

Auramycinone and its glycosides have a three hydrogen singlet between 1.39 and 1.47 ppm. This suits to be the methyl group of position 13, which is not bound to other hydrogens. This item distinguishes these compounds from aklavinone and its glycosides, wherein the side chain is ethyl.

The 8-position CH$_2$-hydrogens of auramycinone and its glycosides give one doublet at 2.2 ppm and a double doublet at 2.6 ppm. In addition, in the spectra of Compounds III and IV peaks corresponding to their sugars are found.

The H-NMR results match well with the structures given in the Figures.

Deposited Microorganisms

The following microorganism was deposited in Deutsche Samrnlung von Mikroorganismen und Zellkulturen (DSM), Mascheroder Weg 1 b, D-38124 Braunschweig, Germany

| Microorganism | Deposition number | Deposition date |
|---|---|---|
| *Streptomyces lividans* Th24/pSY15 | DSM 9436 | 15 September 1994 |

Scheme I
Structural formulas of the compounds obtained

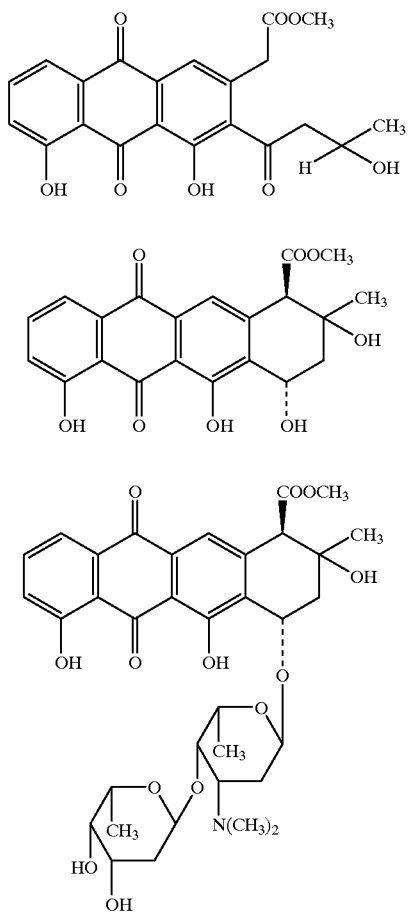

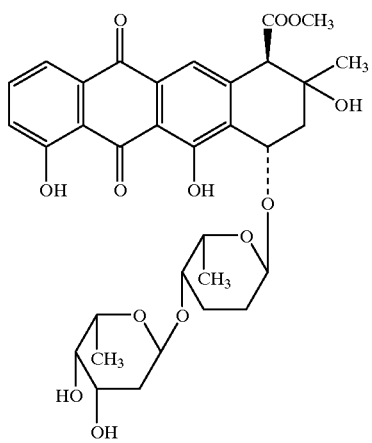

REFERENCES

Arrowsmith, T. J., Malpartida, F., Sherman, D. H., Birch, A., Hopwood, D. A. and Robinson, J. A. 1992. Characterization of actI-homologous DNA encoding polyketide synthase genes from monensin producer *Streptomyces cinnamonensis*. Mol. Gen. Genet. 234: 254–264

Bhuyan, B. K. and Dietz, A. 1965. Fermentation, taxonomic, and biological studies of nogalamycin. Antimicrob. Agents Chemother. 1965:836–844.

Bibb, M. J., Sherman, D. H., Omura, S. and Hopwood, D. A. 1994 Cloning, sequencing and deduced functions of a cluster of Streptomyces genes probably encoding biosynthesis of the polyketide antibiotic frenolicin. Gene Bibb, M. J. Biro, S., Motamedi, H., Collins, J. F. and Hutchinson, C. R. 1989. Analysis of the nucleotide sequence of the *Streptomyces glaucescens* tcmI genes provides key information about the enzymology of polyketide antibiotic biosynthesis. EMBO J. 8: 2727–2736.

Dower W. J., Miller, J. F. and Ragsdale, C. W. 1988. High efficiency transformation of *E.coli* by high voltage electroporation. Nucleic Acids Research 16:6127–6145.

Fernandez-Moreno, M. A., Martinez, E., Boto, L., Hopwood, D. A. and Malpartida, F. 1992. Nucleotide sequence and deduced functions of a set of cotranscribed genes of *Streptomyces coelicolor* A3(2) including the polyketide synthase for the antibiotic actinorhodin. J.Biol.Chem. 267: 19278–19290

Floss, H. G. (1987) Hybrid antibiotics—the contribution of the new gene cornbinations. Trends in Biotech. 5:111–115.

Fujivara, A. and Hoshino, T. 1986. Anthracycline antibiotics. CRC critical reviews in biotechnology. 3:2:133–157.

Gräfe, U, Dornberger, K., Wagner, C and Eckardt, K. 1989. Advances in bioconversion of anthracycline antibiotics. Biotech. Adv. 7:215–239.

Hallam, S. E., Malpartida, F. and Hopwood, D. A. 1988. Nucleotide sequence, transcription and deduced function of a gene involved in polyketide antibiotic synthesis in *Streptomyces coelicolor*. Gene 74:305–320.

Hopwood, D. A., M. J. Bibb, K. F. Chater, T. Kieser, C. J. Bruton, H. M. Kieser, D. J. Lydiate, C. P. Smith, J. M. Ward, and H. Schrempf. 1985. Genetic manipulations of Streptomyces: a laboratory manual. The John Innes Foundation, Norwich, United Kingdom.

Katz, L., and Donadio, S. 1993. Polyketide synthesis: prospects for hybrid antibiotics. Annu. Rev. Microbiol. 47:875–912.

Kim, E-S., Bibb, M. J., Butler, M. J., Hopwood, D. A. and Sherman, D. H. 1994. Nucleotide sequence of the oxytetracycline (otc) polyketide synthase genes from Streptomyces rimosus. Gene 141:141–142.

Malpartida, F. and Hopwood, D. A. 1984. Molecular cloning of the whole biosynthetic pathway of a Streptomyces antibiotic and its expression in a heterologous host. Nature 309:462–464.

Malpartida, F., S. E. Hallam, H. M. Kieser, H. Motamedi, C. R. Hutchinson, M. J. Butler, D. A. Sugden, M. Warren, C.McKillop, C. R. Bailey, G. O. Humphreys, and D. A. Hopwood. 1987. Homology between Streptomyces genes coding for synthesis of different polyketides used to clone antibiotic synthesis genes. Nature (London) 325:818–821.

McDaniel, R., S. Ebert-Khosla, D. A. Hopwood, and C. Khosla. 1993. Engineered biosynthesis of novel polyketides. Science 262:1546–1550.

Niemi, J., K. Ylihonko, J. Hakala, R. Pärssinen, A. Kopio, and P. Mäntsälä. 1994. Hybrid anthracycline antibiotics: production of new anthracyclines by cloned genes from *Streptomyces purpurascens* in *Streptomyces galilaeus*. Microbiol. 140:1351–1358.

Sambrook, J., E. F. Fritsch, and T.Maniatis. 1989. Molecular cloning: a laboratory manual, 2nd ed. Cold Spring Harbor Laboratory Press, Cold Spring Harbor, N. Y.

Shen, B. and Hutchinson, R. 1993. Enzymatic synthesis of a bacterial polyketide from acetyl and malonyl Coenzyme A. Science 262:1535–1540.

Sherman, D. H., Malpartida, F., Bibb, M. J., Kieser, H. M. and Hopwood, D. A. 1989. Structure and deduced function of the granaticin-producing polyketide synthase gene cluster of *Streptomyces violaceoruber* Tü22. EMBO J. 8: 2717–2725.

Ward, J. M, G. R. Janssen, T. Kieser, M. J. Bibb, M. J. Buttner and M. J. Bibb. 1986. Construction and charaterization of a series of multi-copy promoter-probe plasnid vectors for Streptomyces using the aminoglycoside phosphotransferase from Tn5 as indicator. Mol. Gen. Genet. 203:468–478.

Ylihonko, K., J. Hakala, J. Niemi, J. Lundell and P. Mäntsälä. 1994. Isolation and characterization of aclacinomycin A-nonproducing *Streptomyces galilaeus* (ATCC 31615) mutants. Microbiol. 140:1359–1365.

Yu, T.-W., Bibb, M. J., Revill, W. P. and Hopwood, D. A. 1994. Cloning, sequencing and analysis of the griseusin polyketide synthase gene cluster from *Streptomyces griseus*. J. Bacteriol. 176:2627–2634.

What is claim is:

1. An isolated and purified DNA fragment, which is the actI-hybridizing 12 kb BglII-BglII-fragment encoding anthracycline biosynthetic pathway genes of the bacterium *Streptomyces nogalater*.

2. The DNA fragment according to claim 1, comprising the nucleotide sequence given in SEQ ID NO: 1, or a fragment thereof encoding at least one gene of the anthracycline biosynthetic pathway.

3. A recombinant DNA comprising the DNA fragment according to claim 2, included in a plasmid, wherein the plasmid can be transferred in to a Streptomyces bacterium and is copied therein.

4. The recombinant DNA according to claim 3, wherein the plasmid is plasmid pSY15 deposited in *S. lividans* strain TK24/pSY15 at DSM-Deutsche Sammlung Von Mikroorganismen und Zellkulturen, Braunschweig, Germany, with the deposition number DSM 9436.

5. A recombinant DNA comprising the DNA fragment according to claim 1, included in a plasmid, wherein the plasmid can be transferred to a Streptomyces bacterium and is copied therein.

6. A process for the production of anthracyclines comprising transferring the DNA fragment according to claim 1 into a *Streptomyces galilaeus* host cultivating the recombinant strain obtained, and isolating the products formed.

7. A process according to claim 6, wherein the DNA fragment comprises the fragment of claim 2.

8. The process according to claim 7, wherein the anthracycline is auramycinone or a glycoside thereof, and wherein the host is a non-producing mutant strain of *Streptomyces galilaeus*.

9. The process according to claim 8, wherein the *Streptomyces galilaeus* host is the strain H028 which is a mutant strain of *S. galilaeus* ATCC 31615.

10. A process according to claim 6, wherein the anthracycline is auramycinone or a glycoside thereof, and wherein the host is a non-producing mutant strain of *Streptomyces galilaeus*.

11. The process according to claim 10, wherein the *Streptomyces galiaeus* host is the strain H028 which is a mutant strain of *S. galilaeus* ATCC 31615.

12. A process for the production of precursors of anthracyclines, comprising transferring the DNA fragment according to claim 1 into a *Streptomyces lividans* host, cultivating the recombinant strain obtained, and isolating the products formed.

13. The process according to claim 12, wherein the DNA fragment comprises the fragment of claim 11.

14. A process according to claim 12, wherein an anthracycline precursor is produced, which has the following formula:

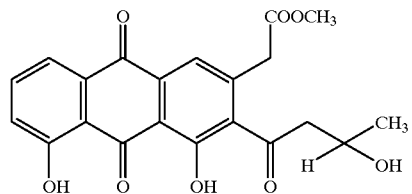

* * * * *

SEQUENCE LISTING

```
(1) GENERAL INFORMATION:

(iii) NUMBER OF SEQUENCES: 7

(2) INFORMATION FOR SEQ ID NO: 1:

(i) SEQUENCE CHARACTERISTICS:
        (A) LENGTH: 3252 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (B) STRAIN: Streptomyces nogalater ATCC 27451

(ix) FEATURE:
        (A) NAME/KEY: CDS
        (B) LOCATION: 359..1651
        (D) OTHER INFORMATION: /note= "ORF1"

(ix) FEATURE:
        (A) NAME/KEY: CDS
        (B) LOCATION: 2937..3197
        (D) OTHER INFORMATION: /note= "ORF3"

(ix) FEATURE:
        (A) NAME/KEY: misc_feature
        (B) LOCATION: 1648..1651
        (D) OTHER INFORMATION: /note= "overlapping sequence in
            ORF1 and ORF2"

(xi) SEQUENCE DESCRIPTION: SEQ ID NO: 1:

GAATTCGGCC GTACCCCGAC GGCCGATTCC TTACCCTTCC GGAGCGGCTT GCGGATCGCA      60

GGACGAAGTC CTCCCTCTCC CCCCATCGGG CGTCCGCTCT TTGTGACCGG TTCACGAGTC     120

GGGTTCCAGC GCTCCTCGAC TCAGGATCGA CCCCTTCCGC GGTAGCCGCC CCGCAGGAAC     180
```

```
CGCAAACCTT CCGCGCCGGT CCCGCCGGGC TTCGCCGCAC CCGTCCATCC GTCATTGAGC      240

TGATTTCGAG ACAGGACGCG CACTGTCACC ACGAGCCCTG TGCGGTTGAA GTCATCACCT      300

GTCCGCGCAC AGGAACTTCA AGACGATCAA AGCCCCTAGT GAAGGGCATC TTCGACGA       358

ATG AAG GAA TCC ATC AAC CGT CGC GTG GTC ATC ACC GGA ATA GGG ATC       406
Met Lys Glu Ser Ile Asn Arg Arg Val Val Ile Thr Gly Ile Gly Ile
 1               5                  10                  15

GTC GCG CCC GAT GCC ACC GGG GTG AAA CCG TTC TGG GAT CTG CTG ACG       454
Val Ala Pro Asp Ala Thr Gly Val Lys Pro Phe Trp Asp Leu Leu Thr
                 20                  25                  30

GCC GGT CGC ACC GCG ACC CGG ACC ATC ACC GCC TTC GAT CCC TCT CCG       502
Ala Gly Arg Thr Ala Thr Arg Thr Ile Thr Ala Phe Asp Pro Ser Pro
             35                  40                  45

TTC CGT TCC CGC ATC GCC GCG GAA TGC GAT TTC GAC CCG CTT GCC GAA       550
Phe Arg Ser Arg Ile Ala Ala Glu Cys Asp Phe Asp Pro Leu Ala Glu
 50                  55                  60

GGG CTG ACC CCC CAG CAG ATC CGG CGT ATG GAC CGG GCC ACG CAG TTC       598
Gly Leu Thr Pro Gln Gln Ile Arg Arg Met Asp Arg Ala Thr Gln Phe
 65                  70                  75                  80

GCG GTC GTC AGC GCC CGG GAA AGC CTG GAG GAC AGC GGA CTC GAC CTC       646
Ala Val Val Ser Ala Arg Glu Ser Leu Glu Asp Ser Gly Leu Asp Leu
                     85                  90                  95

GGC GCC CTG GAC GCC TCC CGC ACC GGC GTG GTC GTC GGC AGC GCG GTC       694
Gly Ala Leu Asp Ala Ser Arg Thr Gly Val Val Val Gly Ser Ala Val
                 100                 105                 110

GGC TGC ACC ACG AGC CTG GAA GAG GAG TAC GCG GTC GTC AGC GAC AGC       742
Gly Cys Thr Thr Ser Leu Glu Glu Glu Tyr Ala Val Val Ser Asp Ser
             115                 120                 125

GGC CGG AAC TGG CTG GTC GAC GAC GGC TAC GCC GTA CCG CAC CTA TTC       790
Gly Arg Asn Trp Leu Val Asp Asp Gly Tyr Ala Val Pro His Leu Phe
 130                 135                 140

GAC TAC TTC GTG CCC AGC TCC ATC GCC GCC GAG GTG GCA CAC GAC CGC       838
Asp Tyr Phe Val Pro Ser Ser Ile Ala Ala Glu Val Ala His Asp Arg
 145                 150                 155                 160

ATC GGC GCG GAG GGC CCC GTC AGC CTC GTG TCG ACC GGG TGC ACC TCG       886
Ile Gly Ala Glu Gly Pro Val Ser Leu Val Ser Thr Gly Cys Thr Ser
                 165                 170                 175

GGC CTG GAC GCC GTG GGC CGC GCG GCC GAC CTG ATC GCC GAG GGA GCG       934
Gly Leu Asp Ala Val Gly Arg Ala Ala Asp Leu Ile Ala Glu Gly Ala
             180                 185                 190

GCG GAT GTG ATG CTG GCC GGT GCG ACC GAG GCG CCC ATC TCC CCC ATC       982
Ala Asp Val Met Leu Ala Gly Ala Thr Glu Ala Pro Ile Ser Pro Ile
         195                 200                 205

ACC GTG GCG TGC TTC GAT GCC ATC AAG GCG ACC ACC CCC CGC AAC GAC      1030
Thr Val Ala Cys Phe Asp Ala Ile Lys Ala Thr Thr Pro Arg Asn Asp
 210                 215                 220

ACG CCC GCC GAG GCG TCC CGT CCG TTC GAC CGC ACC AGG AAC GGG TTC      1078
Thr Pro Ala Glu Ala Ser Arg Pro Phe Asp Arg Thr Arg Asn Gly Phe
225                  230                 235                 240

GTA CTC GGC GAG GGC GCT GCC GTG TTC GTC CTG GAG GAG TTC GAA CAC      1126
Val Leu Gly Glu Gly Ala Ala Val Phe Val Leu Glu Glu Phe Glu His
                 245                 250                 255

GCG CGC CGC CGG GGC GCG CTC GTG TAC GCG GAG ATC GCC GGG TTC GCC      1174
Ala Arg Arg Arg Gly Ala Leu Val Tyr Ala Glu Ile Ala Gly Phe Ala
             260                 265                 270

ACT CGC TGC AAC GCC TTC CAC ATG ACC GGT CTG CGC CCG GAC GGG CGG      1222
Thr Arg Cys Asn Ala Phe His Met Thr Gly Leu Arg Pro Asp Gly Arg
         275                 280                 285

GAG ATG GCG GAG GCC ATC GGG GTG GCG CTC GCC CAG GCG GGC AAG GCG      1270
```

```
Glu Met Ala Glu Ala Ile Gly Val Ala Leu Ala Gln Ala Gly Lys Ala
    290                 295                 300

CCG GCT GAC GTC GAC TAC GTC AAC GCC CAC GGT TCC GGC ACC CGG CAG      1318
Pro Ala Asp Val Asp Tyr Val Asn Ala His Gly Ser Gly Thr Arg Gln
305                 310                 315                 320

AAT GAC CGT CAC GAG ACG GCG GCC TTC AAG CGC AGT CTC GGC GAC CAC      1366
Asn Asp Arg His Glu Thr Ala Ala Phe Lys Arg Ser Leu Gly Asp His
                325                 330                 335

GCC TAC CGG GTC CCG GTC AGC AGC ATC AAA TCC ATG ATC GGG CAC TCG      1414
Ala Tyr Arg Val Pro Val Ser Ser Ile Lys Ser Met Ile Gly His Ser
                340                 345                 350

CTG GGC GCG ATC GGC TCC CTG GAG ATC GCC GCC TCC GTG CTG GCC ATC      1462
Leu Gly Ala Ile Gly Ser Leu Glu Ile Ala Ala Ser Val Leu Ala Ile
                355                 360                 365

ACA CAC GAC GTG GTG CCG CCC ACC GCC AAT CTG CAC GAG CCG GAT CCC      1510
Thr His Asp Val Val Pro Pro Thr Ala Asn Leu His Glu Pro Asp Pro
370                 375                 380

GAG TGC GAT CTG GAC TAC GTG CCG CTG CGG GCG CGT GCG TGC CCG GTG      1558
Glu Cys Asp Leu Asp Tyr Val Pro Leu Arg Ala Arg Ala Cys Pro Val
385                 390                 395                 400

GAC ACG GTG CTC ACG GTG GGC AGC GGG TTC GGC GGT TTC CAG AGC GCC      1606
Asp Thr Val Leu Thr Val Gly Ser Gly Phe Gly Gly Phe Gln Ser Ala
                405                 410                 415

ATG GTG CTG TGC GGT CCG GGC TCG CGG GGA AGG TCG GCC GCG TGACGGCCGC   1658
Met Val Leu Cys Gly Pro Gly Ser Arg Gly Arg Ser Ala Ala
                420                 425                 430

CGTGGTGGTG ACCGGTCTCG GCGTCGTCGC CCCCACCGGT CTCGGGTGC GGGAGCACTG     1718

GTCGAGTACG GTCCGGGGGG CGTCGGCGAT CGGACCGGTC ACCCGGTTCG ACGCCGGCCG    1778

GTACCCCAGC AAACTGGCCG GAGAGGTGCC CGGTTTCGTC CCGGAGGACC ATCTGCCCAG    1838

CCGGCTGATG CCGCAGACGG ACCATATGAC GCGCCTGGCG CTCGTCGCGG CGGACTGGGC    1898

CTTCCAGGAC GCCGCCGTGG ACCCGTCGAA GCTGCCGGAG TACGGCGTCG GCGTGGTCAC    1958

CGCGAGTTCG GCGGGGGGGT TCGAATTCGG CCACCGCGAG CTGCAGAACC TGTGGAGCCT    2018

GGGCCCGCAG TACGTCAGCG CGTATCAGTC GTTCGCATGG TTCTATGCCG TGAACACCGG    2078

TCAGGTGTCC ATCCGGCACG GGCTGCGCGG CCCGGGCGGG GTGCTGGTGA CGGAACAGGC    2138

GGGCGGCCTG GACGCCCTTG GCAGGCCCG GCGGCAGTTG CGGCGCGGAC TGCCGATGGT    2198

GGTCGCGGGA GCCGTTGACG GCTCGCCCTG CCCCTGGGGC TGGGTGGCGC AGCTCAGCTC    2258

GGGCGGCCTC AGCACGTCGG ACGACCCGCG CCGGGCCTAT CTGCCGTTCG ACGCCGCAGC    2318

CGGCGGACAC GTGCCGGGAG AGGGCGGCGC CCTGCTCGTC CTGGAGAGCG ACGAGTCGGC    2378

CCGGGCGCGC GGGGTGACGC GGTGGTACGG GCGCATCGAT GGGTACGCCG CCACATTCGA    2438

CCCCCCGCCC GGTTCGGGGC GCCCGCCGAA CCTGCTGCGG GCCGCGCAGG CGGCACTGGA    2498

CGACGCGGAG GTCGGACCCG AGGCGGTCGA CGTGGTGTTC GCGGACGCGT CCGGCACCCC    2558

GGACGAGGAC GCGGCGGAGG CCGACGCGGT GCGGCGCCTG TTCGGACCGT ACGGCGTTCC    2618

GGTGACGGCG CCGAAGACCA TGACCGGCCG CCTCAGCGCG GCGGCGCGG CCCTCGACGT     2678

GGCGACGGCG CTGCTGGCGC TGCGCGAGGG CGTCGTCCCG CCGACGGTCA ACGTCTCCCG    2738

GCCGCGGCCG GAGTACGAGC TGGACCTGGT GCTCGCCCCC CGGCGCACGC CCCTGGCCAG    2798

GGCCCTGGTG CTCGCGCGGG CCGGGGCGG GTTCAATGCG GCGATGGTCG TGGCGGGGCC     2858

GCGCGCGGAG ACACGGTGAA GCGGCCCGGC GCAGCCGGAG CCGCGGTAAG AGGCCACGGA    2918

AGAGAGAGGG ATGCGACG GTG AAG CAG CAG CTG ACG ACG GAA CGG CTC ATG     2969
             Val Lys Gln Gln Leu Thr Thr Glu Arg Leu Met
              1               5                   10
```

```
GAG ATC ATG CGG GAG TGC GCG GGC TAC GGT GAG GAC GTC GAC GCT CTG          3017
Glu Ile Met Arg Glu Cys Ala Gly Tyr Gly Glu Asp Val Asp Ala Leu
         15                  20                  25

GGC GAC ACG GAC GGC GCC GAC TTC GCC GCA CTC GGC TAC GAC TCG CTG          3065
Gly Asp Thr Asp Gly Ala Asp Phe Ala Ala Leu Gly Tyr Asp Ser Leu
             30                  35                  40

GCG CTC CTG GAA ACG GCC GGC CGG CTC GAG CGC GAG TTC GGC ATC CAG          3113
Ala Leu Leu Glu Thr Ala Gly Arg Leu Glu Arg Glu Phe Gly Ile Gln
 45                  50                  55

CTC GGT GAC GAG GTG GTC GCC GAC GCC AGG ACG CCT GCC GAG CTG ACC          3161
Leu Gly Asp Glu Val Val Ala Asp Ala Arg Thr Pro Ala Glu Leu Thr
 60                  65                  70                  75

GCC CTG GTC AAC CGG ACG GTG GCC GAG GCG GCC TGACCCGGCC GGCCCACGAG        3214
Ala Leu Val Asn Arg Thr Val Ala Glu Ala Ala
                 80                  85

AGCGGGGTGA CGCGTGTGTA CGGCACGGAA CTCACACA                                3252

(2) INFORMATION FOR SEQ ID NO: 2:

(i) SEQUENCE CHARACTERISTICS:
        (A) LENGTH: 430 amino acids
        (B) TYPE: amino acid
        (D) TOPOLOGY: linear (ii) MOLECULE TYPE: protein (xi) SEQUENCE DESCRIPTION: SEQ ID NO: 2:

Met Lys Glu Ser Ile Asn Arg Arg Val Val Ile Thr Gly Ile Gly Ile
 1               5                  10                  15

Val Ala Pro Asp Ala Thr Gly Val Lys Pro Phe Trp Asp Leu Leu Thr
             20                  25                  30

Ala Gly Arg Thr Ala Thr Arg Thr Ile Thr Ala Phe Asp Pro Ser Pro
         35                  40                  45

Phe Arg Ser Arg Ile Ala Ala Glu Cys Asp Phe Asp Pro Leu Ala Glu
 50                  55                  60

Gly Leu Thr Pro Gln Gln Ile Arg Arg Met Asp Arg Ala Thr Gln Phe
 65                  70                  75                  80

Ala Val Val Ser Ala Arg Glu Ser Leu Glu Asp Ser Gly Leu Asp Leu
                 85                  90                  95

Gly Ala Leu Asp Ala Ser Arg Thr Gly Val Val Gly Ser Ala Val
             100                 105                 110

Gly Cys Thr Thr Ser Leu Glu Glu Tyr Ala Val Val Ser Asp Ser
             115                 120                 125

Gly Arg Asn Trp Leu Val Asp Asp Gly Tyr Ala Val Pro His Leu Phe
 130                 135                 140

Asp Tyr Phe Val Pro Ser Ser Ile Ala Ala Glu Val Ala His Asp Arg
 145                 150                 155                 160

Ile Gly Ala Glu Gly Pro Val Ser Leu Val Ser Thr Gly Cys Thr Ser
             165                 170                 175

Gly Leu Asp Ala Val Gly Arg Ala Ala Asp Leu Ile Ala Glu Gly Ala
             180                 185                 190

Ala Asp Val Met Leu Ala Gly Ala Thr Glu Ala Pro Ile Ser Pro Ile
             195                 200                 205

Thr Val Ala Cys Phe Asp Ala Ile Lys Ala Thr Thr Pro Arg Asn Asp
 210                 215                 220

Thr Pro Ala Glu Ala Ser Arg Pro Phe Asp Arg Thr Arg Asn Gly Phe
 225                 230                 235                 240
```

```
Val Leu Gly Glu Gly Ala Ala Val Phe Val Leu Glu Glu Phe Glu His
            245                 250                 255

Ala Arg Arg Arg Gly Ala Leu Val Tyr Ala Glu Ile Ala Gly Phe Ala
            260                 265                 270

Thr Arg Cys Asn Ala Phe His Met Thr Gly Leu Arg Pro Asp Gly Arg
            275                 280                 285

Glu Met Ala Glu Ala Ile Gly Val Ala Leu Ala Gln Ala Gly Lys Ala
            290                 295                 300

Pro Ala Asp Val Asp Tyr Val Asn Ala His Gly Ser Gly Thr Arg Gln
305                 310                 315                 320

Asn Asp Arg His Glu Thr Ala Ala Phe Lys Arg Ser Leu Gly Asp His
            325                 330                 335

Ala Tyr Arg Val Pro Val Ser Ser Ile Lys Ser Met Ile Gly His Ser
            340                 345                 350

Leu Gly Ala Ile Gly Ser Leu Glu Ile Ala Ala Ser Val Leu Ala Ile
            355                 360                 365

Thr His Asp Val Val Pro Pro Thr Ala Asn Leu His Glu Pro Asp Pro
            370                 375                 380

Glu Cys Asp Leu Asp Tyr Val Pro Leu Arg Ala Arg Ala Cys Pro Val
385                 390                 395                 400

Asp Thr Val Leu Thr Val Gly Ser Gly Phe Gly Gly Phe Gln Ser Ala
            405                 410                 415

Met Val Leu Cys Gly Pro Gly Ser Arg Gly Arg Ser Ala Ala
            420                 425                 430

(2) INFORMATION FOR SEQ ID NO: 3:

(i) SEQUENCE CHARACTERISTICS:
        (A) LENGTH: 86 amino acids
        (B) TYPE: amino acid
        (D) TOPOLOGY: linear (ii) MOLECULE TYPE: protein (xi) SEQUENCE DESCRIPTION: SEQ ID NO: 3:

Val Lys Gln Gln Leu Thr Thr Glu Arg Leu Met Glu Ile Met Arg Glu
 1               5                  10                  15

Cys Ala Gly Tyr Gly Glu Asp Val Asp Ala Leu Gly Asp Thr Asp Gly
            20                  25                  30

Ala Asp Phe Ala Ala Leu Gly Tyr Asp Ser Leu Ala Leu Leu Glu Thr
            35                  40                  45

Ala Gly Arg Leu Glu Arg Glu Phe Gly Ile Gln Leu Gly Asp Glu Val
            50                  55                  60

Val Ala Asp Ala Arg Thr Pro Ala Glu Leu Thr Ala Leu Val Asn Arg
65                  70                  75                  80

Thr Val Ala Glu Ala Ala
            85

(2) INFORMATION FOR SEQ ID NO: 4:

(i) SEQUENCE CHARACTERISTICS:
        (A) LENGTH: 3252 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO
```

(vi) ORIGINAL SOURCE:
    (B) STRAIN: Streptomyces nogalater ATCC 27451

(ix) FEATURE:
    (A) NAME/KEY: CDS
    (B) LOCATION: 1648..2877
    (D) OTHER INFORMATION: /note= "ORF2"

(xi) SEQUENCE DESCRIPTION: SEQ ID NO: 4:

```
GAATTCGGCC GTACCCCGAC GGCCGATTCC TTACCCTTCC GGAGCGGCTT GCGGATCGCA    60

GGACGAAGTC CTCCCTCTCC CCCCATCGGG CGTCCGCTCT TTGTGACCGG TTCACGAGTC   120

GGGTTCCAGC GCTCCTCGAC TCAGGATCGA CCCCTTCCGC GGTAGCCGCC CCGCAGGAAC   180

CGCAAACCTT CCGCGCCGGT CCCGCCGGGC TTCGCCGCAC CCGTCCATCC GTCATTGAGC   240

TGATTTCGAG ACAGGACGCG CACTGTCACC ACGAGCCCTG TGCGGTTGAA GTCATCACCT   300

GTCCGCGCAC AGGAACTTCA AGACGATCAA AGCCCCTAGT GAAGGGCATC TTCGACGAAT   360

GAAGGAATCC ATCAACCGTC GCGTGGTCAT CACCGGAATA GGGATCGTCG CGCCCGATGC   420

CACCGGGGTG AAACCGTTCT GGGATCTGCT GACGGCCGGT CGCACCGCGA CCCGGACCAT   480

CACCGCCTTC GATCCCTCTC CGTTCCGTTC CCGCATCGCC GCGGAATGCG ATTTCGACCC   540

GCTTGCCGAA GGGCTGACCC CCAGCAGAT CCGGCGTATG GACCGGGCCA CGCAGTTCGC   600

GGTCGTCAGC GCCCGGGAAA GCCTGGAGGA CAGCGGACTC GACCTCGGCG CCCTGGACGC   660

CTCCCGCACC GGCGTGGTCG TCGGCAGCGC GGTCGGCTGC ACCACGAGCC TGGAAGAGGA   720

GTACGCGGTC GTCAGCGACA GCGGCCGGAA CTGGCTGGTC GACGACGGCT ACGCCGTACC   780

GCACCTATTC GACTACTTCG TGCCCAGCTC CATCGCCGCC GAGGTGGCAC ACGACCGCAT   840

CGGCGCGGAG GGCCCCGTCA GCCTCGTGTC GACCGGGTGC ACCTCGGGCC TGGACGCCGT   900

GGGCCGCGCG GCCGACCTGA TCGCCGAGGG AGCGGCGGAT GTGATGCTGG CCGGTGCGAC   960

CGAGGCGCCC ATCTCCCCCA TCACCGTGGC GTGCTTCGAT GCCATCAAGG CGACCACCCC  1020

CCGCAACGAC ACGCCCGCCG AGGCGTCCCG TCCGTTCGAC CGCACCAGGA ACGGGTTCGT  1080

ACTCGGCGAG GGCGCTGCCG TGTTCGTCCT GGAGGAGTTC GAACACGCGC GCCGCCGGGG  1140

CGCGCTCGTG TACGCGGAGA TCGCCGGGTT CGCCACTCGC TGCAACGCCT TCCACATGAC  1200

CGGTCTGCGC CCGGACGGGC GGGAGATGGC GGAGGCCATC GGGGTGGCGC TCGCCCAGGC  1260

GGGCAAGGCG CCGGCTGACG TCGACTACGT CAACGCCCAC GGTTCCGGCA CCCGGCAGAA  1320

TGACCGTCAC GAGACGGCGG CCTTCAAGCG CAGTCTCGGC GACCACGCCT ACCGGGTCCC  1380

GGTCAGCAGC ATCAAATCCA TGATCGGGCA CTCGCTGGGC GCGATCGGCT CCCTGGAGAT  1440

CGCCGCCTCC GTGCTGGCCA TCACACACGA CGTGGTGCCG CCCACCGCCA ATCTGCACGA  1500

GCCGGATCCC GAGTGCGATC TGGACTACGT GCCGCTGCGG GCGCGTGCGT GCCCGGTGGA  1560

CACGGTGCTC ACGGTGGGCA GCGGGTTCGG CGGTTTCCAG AGCGCCATGG TGCTGTGCGG  1620

TCCGGGCTCG CGGGGAAGGT CGGCCGC GTG ACG GCC GCC GTG GTG GTG ACC      1671
                              Val Thr Ala Ala Val Val Val Thr
                                1               5

GGT CTC GGC GTC GTC GCC CCC ACC GGT CTC GGG GTG CGG GAG CAC TGG    1719
Gly Leu Gly Val Val Ala Pro Thr Gly Leu Gly Val Arg Glu His Trp
    10              15                  20

TCG AGT ACG GTC CGG GGG GCG TCG GCG ATC GGA CCG GTC ACC CGG TTC    1767
Ser Ser Thr Val Arg Gly Ala Ser Ala Ile Gly Pro Val Thr Arg Phe
25              30                  35                  40

GAC GCC GGC CGG TAC CCC AGC AAA CTG GCC GGA GAG GTG CCC GGT TTC    1815
Asp Ala Gly Arg Tyr Pro Ser Lys Leu Ala Gly Glu Val Pro Gly Phe
            45                  50                  55
```

```
GTC CCG GAG GAC CAT CTG CCC AGC CGG CTG ATG CCG CAG ACG GAC CAT    1863
Val Pro Glu Asp His Leu Pro Ser Arg Leu Met Pro Gln Thr Asp His
             60                  65                  70

ATG ACG CGC CTG GCG CTC GTC GCG GCG GAC TGG GCC TTC CAG GAC GCC    1911
Met Thr Arg Leu Ala Leu Val Ala Ala Asp Trp Ala Phe Gln Asp Ala
         75                  80                  85

GCC GTG GAC CCG TCG AAG CTG CCG GAG TAC GGC GTC GGC GTG GTC ACC    1959
Ala Val Asp Pro Ser Lys Leu Pro Glu Tyr Gly Val Gly Val Val Thr
     90                  95                 100

GCG AGT TCG GCG GGG GGG TTC GAA TTC GGC CAC CGC GAG CTG CAG AAC    2007
Ala Ser Ser Ala Gly Gly Phe Glu Phe Gly His Arg Glu Leu Gln Asn
105                 110                 115                 120

CTG TGG AGC CTG GGC CCG CAG TAC GTC AGC GCG TAT CAG TCG TTC GCA    2055
Leu Trp Ser Leu Gly Pro Gln Tyr Val Ser Ala Tyr Gln Ser Phe Ala
             125                 130                 135

TGG TTC TAT GCC GTG AAC ACC GGT CAG GTG TCC ATC CGG CAC GGG CTG    2103
Trp Phe Tyr Ala Val Asn Thr Gly Gln Val Ser Ile Arg His Gly Leu
         140                 145                 150

CGC GGC CCG GGC GGG GTG CTG GTG ACG GAA CAG GCG GGC GGC CTG GAC    2151
Arg Gly Pro Gly Gly Val Leu Val Thr Glu Gln Ala Gly Gly Leu Asp
     155                 160                 165

GCC CTT GGG CAG GCC CGG CGG CAG TTG CGG CGC GGA CTG CCG ATG GTG    2199
Ala Leu Gly Gln Ala Arg Arg Gln Leu Arg Arg Gly Leu Pro Met Val
170                 175                 180

GTC GCG GGA GCC GTT GAC GGC TCG CCC TGC CCC TGG GGC TGG GTG GCG    2247
Val Ala Gly Ala Val Asp Gly Ser Pro Cys Pro Trp Gly Trp Val Ala
185                 190                 195                 200

CAG CTC AGC TCG GGC GGC CTC AGC ACG TCG GAC GAC CCG CGC CGG GCC    2295
Gln Leu Ser Ser Gly Gly Leu Ser Thr Ser Asp Asp Pro Arg Arg Ala
             205                 210                 215

TAT CTG CCG TTC GAC GCC GCA GCC GGC GGA CAC GTG CCG GGA GAG GGC    2343
Tyr Leu Pro Phe Asp Ala Ala Ala Gly Gly His Val Pro Gly Glu Gly
         220                 225                 230

GGC GCC CTG CTC GTC CTG GAG AGC GAC GAG TCG GCC CGG GCG CGC GGG    2391
Gly Ala Leu Leu Val Leu Glu Ser Asp Glu Ser Ala Arg Ala Arg Gly
     235                 240                 245

GTG ACG CGG TGG TAC GGG CGC ATC GAT GGG TAC GCC GCC ACA TTC GAC    2439
Val Thr Arg Trp Tyr Gly Arg Ile Asp Gly Tyr Ala Ala Thr Phe Asp
250                 255                 260

CCC CCG CCC GGT TCG GGG CGC CCG CCG AAC CTG CTG CGG GCC GCG CAG    2487
Pro Pro Pro Gly Ser Gly Arg Pro Pro Asn Leu Leu Arg Ala Ala Gln
265                 270                 275                 280

GCG GCA CTG GAC GAC GCG GAG GTC GGA CCC GAG GCG GTC GAC GTG GTG    2535
Ala Ala Leu Asp Asp Ala Glu Val Gly Pro Glu Ala Val Asp Val Val
             285                 290                 295

TTC GCG GAC GCG TCC GGC ACC CCG GAC GAG GAC GCG GCG GAG GCC GAC    2583
Phe Ala Asp Ala Ser Gly Thr Pro Asp Glu Asp Ala Ala Glu Ala Asp
         300                 305                 310

GCG GTG CGG CGC CTG TTC GGA CCG TAC GGC GTT CCG GTG ACG GCG CCG    2631
Ala Val Arg Arg Leu Phe Gly Pro Tyr Gly Val Pro Val Thr Ala Pro
     315                 320                 325

AAG ACC ATG ACC GGC CGC CTC AGC GCG GGC GGC GCG GCC CTC GAC GTG    2679
Lys Thr Met Thr Gly Arg Leu Ser Ala Gly Gly Ala Ala Leu Asp Val
330                 335                 340

GCG ACG GCG CTG CTG GCG CTG CGC GAG GGC GTC GTC CCG CCG ACG GTC    2727
Ala Thr Ala Leu Leu Ala Leu Arg Glu Gly Val Val Pro Pro Thr Val
345                 350                 355                 360

AAC GTC TCC CGG CCG CGG CCG GAG TAC GAG CTG GAC CTG GTG CTC GCC    2775
Asn Val Ser Arg Pro Arg Pro Glu Tyr Glu Leu Asp Leu Val Leu Ala
             365                 370                 375
```

-continued

```
CCC CGG CGC ACG CCC CTG GCC AGG GCC CTG GTG CTC GCG CGG GGC CGG    2823
Pro Arg Arg Thr Pro Leu Ala Arg Ala Leu Val Leu Ala Arg Gly Arg
        380                 385                 390

GGC GGG TTC AAT GCG GCG ATG GTC GTG GCG GGG CCG CGC GCG GAG ACA    2871
Gly Gly Phe Asn Ala Ala Met Val Val Ala Gly Pro Arg Ala Glu Thr
        395                 400                 405

CGG TGAAGCGGCC CGGCGCAGCC GGAGCCGCGG TAAGAGGCCA CGGAAGAGAG         2924
Arg

AGGGATGCGA CGGTGAAGCA GCAGCTGACG ACGGAACGGC TCATGGAGAT CATGCGGGAG  2984

TGCGCGGGCT ACGGTGAGGA CGTCGACGCT CTGGGCGACA CGGACGGCGC CGACTTCGCC  3044

GCACTCGGCT ACGACTCGCT GGCGCTCCTG GAAACGGCCG CCGGCTCGA GCGCGAGTTC   3104

GGCATCCAGC TCGGTGACGA GGTGGTCGCC GACGCCAGGA CGCCTGCCGA GCTGACCGCC  3164

CTGGTCAACC GGACGGTGGC CGAGGCGGCC TGACCCGGCC GGCCCACGAG AGCGGGGTGA  3224

CGCGTGTGTA CGGCACGGAA CTCACACA                                    3252
```

(2) INFORMATION FOR SEQ ID NO: 5:

(i) SEQUENCE CHARACTERISTICS:
        (A) LENGTH: 409 amino acids
        (B) TYPE: amino acid
        (D) TOPOLOGY: linear (ii) MOLECULE TYPE: protein (xi) SEQUENCE DESCRIPTION: SEQ ID NO: 5:

```
Val Thr Ala Ala Val Val Thr Gly Leu Gly Val Val Ala Pro Thr
 1               5                  10                  15

Gly Leu Gly Val Arg Glu His Trp Ser Ser Thr Val Arg Gly Ala Ser
                20                  25                  30

Ala Ile Gly Pro Val Thr Arg Phe Asp Ala Gly Arg Tyr Pro Ser Lys
            35                  40                  45

Leu Ala Gly Glu Val Pro Gly Phe Val Pro Glu Asp His Leu Pro Ser
        50                  55                  60

Arg Leu Met Pro Gln Thr Asp His Met Thr Arg Leu Ala Leu Val Ala
 65                  70                  75                  80

Ala Asp Trp Ala Phe Gln Asp Ala Ala Val Asp Pro Ser Lys Leu Pro
                85                  90                  95

Glu Tyr Gly Val Gly Val Val Thr Ala Ser Ser Ala Gly Gly Phe Glu
            100                 105                 110

Phe Gly His Arg Glu Leu Gln Asn Leu Trp Ser Leu Gly Pro Gln Tyr
        115                 120                 125

Val Ser Ala Tyr Gln Ser Phe Ala Trp Phe Tyr Ala Val Asn Thr Gly
    130                 135                 140

Gln Val Ser Ile Arg His Gly Leu Arg Gly Pro Gly Gly Val Leu Val
145                 150                 155                 160

Thr Glu Gln Ala Gly Gly Leu Asp Ala Leu Gly Gln Ala Arg Arg Gln
                165                 170                 175

Leu Arg Arg Gly Leu Pro Met Val Val Ala Gly Ala Val Asp Gly Ser
            180                 185                 190

Pro Cys Pro Trp Gly Trp Val Ala Gln Leu Ser Ser Gly Gly Leu Ser
        195                 200                 205

Thr Ser Asp Asp Pro Arg Arg Ala Tyr Leu Pro Phe Asp Ala Ala Ala
    210                 215                 220

Gly Gly His Val Pro Gly Glu Gly Gly Ala Leu Leu Val Leu Glu Ser
225                 230                 235                 240
```

```
Asp Glu Ser Ala Arg Ala Arg Gly Val Thr Arg Trp Tyr Gly Arg Ile
            245             250                 255

Asp Gly Tyr Ala Ala Thr Phe Asp Pro Pro Gly Ser Gly Arg Pro
            260             265             270

Pro Asn Leu Leu Arg Ala Ala Gln Ala Ala Leu Asp Asp Ala Glu Val
        275             280             285

Gly Pro Glu Ala Val Asp Val Phe Ala Asp Ala Ser Gly Thr Pro
    290             295             300

Asp Glu Asp Ala Ala Glu Ala Asp Ala Val Arg Arg Leu Phe Gly Pro
305             310             315                 320

Tyr Gly Val Pro Val Thr Ala Pro Lys Thr Met Thr Gly Arg Leu Ser
            325             330                 335

Ala Gly Gly Ala Ala Leu Asp Val Ala Thr Ala Leu Leu Ala Leu Arg
            340             345             350

Glu Gly Val Val Pro Pro Thr Val Asn Val Ser Arg Pro Arg Pro Glu
            355             360             365

Tyr Glu Leu Asp Leu Val Leu Ala Pro Arg Arg Thr Pro Leu Ala Arg
    370             375             380

Ala Leu Val Leu Ala Arg Gly Arg Gly Gly Phe Asn Ala Ala Met Val
385             390             395             400

Val Ala Gly Pro Arg Ala Glu Thr Arg
            405

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GTTTTCCCAG   TCACGAC                                                17

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

CAGGAAACAG   CTATGAC                                                17
```